(12) United States Patent
Habener et al.

(10) Patent No.: US 6,923,959 B2
(45) Date of Patent: Aug. 2, 2005

(54) METHOD OF PRE-INDUCING A STATE OF IMMUNE TOLERANCE BEFORE ORGAN TRANSPLANTATION

(75) Inventors: Joel F. Habener, Newton Centre, MA (US); Henryk Zulewski, Basel (CH); Elizabeth J. Abraham, Quincy, MA (US); Mario Vallejo, Madrid (ES); Denise L. Faustman, Weston, MA (US); Melissa K. Thomas, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 45 days.

(21) Appl. No.: 10/136,891

(22) Filed: May 2, 2002

(65) Prior Publication Data

US 2003/0031657 A1 Feb. 13, 2003

Related U.S. Application Data

(63) Continuation-in-part of application No. 09/731,255, filed on Dec. 6, 2000.
(60) Provisional application No. 60/238,880, filed on Oct. 6, 2000, provisional application No. 60/215,109, filed on Jun. 28, 2000, and provisional application No. 60/169,082, filed on Dec. 6, 1999.

(51) Int. Cl.$^7$ ............................ A61K 35/12; C12N 5/00
(52) U.S. Cl. .................. 424/93.7; 424/93.1; 424/520; 435/1.1; 435/4; 435/325
(58) Field of Search ............................ 435/4, 325, 1.1; 424/93.1, 93.7, 520

(56) References Cited

U.S. PATENT DOCUMENTS

| 5,876,708 A | * | 3/1999 | Sachs ........................ 424/93.1 |
| 6,001,647 A | * | 12/1999 | Peck et al. ................... 435/325 |
| 6,006,752 A | * | 12/1999 | Sykes ......................... 128/898 |
| 6,090,400 A | * | 7/2000 | Elliott ........................ 424/422 |
| 6,146,653 A | * | 11/2000 | Elliott ........................ 424/422 |
| 6,280,957 B1 | * | 8/2001 | Sayegh et al. ................ 435/7.1 |
| 6,412,492 B1 | * | 7/2002 | Sykes ......................... 128/898 |
| 6,703,017 B1 | * | 3/2004 | Peck et al. .................. 424/93.7 |
| 2001/0049827 A1 | * | 12/2001 | Hunter et al. .................. 800/8 |
| 2003/0099622 A1 | * | 5/2003 | Hering et al. ............. 424/93.21 |

FOREIGN PATENT DOCUMENTS

| WO | 97/15310 | 5/1997 | .......... A61K/31/70 |
| WO | 01/39784 | 6/2001 | .......... A61K/35/00 |

OTHER PUBLICATIONS

Shizuru et al. Purified hematopoietic stem cell grafts induce tolerance to alloantigens and can mediate positive and negative T cell selection. Proc Natl Acad Sci USA 97(17): 9555–9560, 2000.*
Geggel et al. Effect of peripheral subepithelial fibrosis on corneal transplant topography. J Cataract Refract Surg 22: 135–138, 1996.*
Meyers et al. Lung transplantation: current status and future prospects. World J Surg 23: 1156–1162, 1999.*
Nenno et al. Cornea transplant statistics in the United States. Refractive & Corneal Surg 7: 467–468, 1991.*
Ossevoort et al. Prolonged skin graft survival by administration of anti–CD80 monoclonal antibody with cyclosporin A. J Immunotherapy 22(5): 381–389, 1999.*
Sun et al. Effect of tacrolimus on hemodynamics and absorption of experimental small intestinal transplants. Transplantation 61: 1447–1450, 1996.*
Wood et al. Reconstructed human skin: transplant, graft of biological dressing? Essays Biochem 29: 65–85, 1995.*
Hauben, DJ. The history of free skin transplant operations. Acta Chir Plast. 27(2):66–70, 1985.*
Lau et al. Lung transplantation at Duke University Medical Center. Clin Transpl. 327–340, 1998.*
Schumacher et al. Transplantation of embryonic porcine mesencephalic tissue in patients with PD. Neurology. 54(5):1042–1050, 2000.*
Reemtsma et al. Renal heretotransplantation in man. Ann Surg. 160:384–410, 1964.*
Starzl et al. Baboon–to–human liver transplantation. Lancet. 341(8837):65–71, 1993.*
Fandrich et al. Preimplantation–stage stem cells induce long–term allogeneic graft acceptance without supplementary host conditioning. Nat Med 8(2): 171–178, 2002.*
Rifle, G. et al. Donor–derived hematopoietic cells in organ transplantation: a major step toward allograft tolerance? Transplantation. 75(9 Suppl):3S–7S, 2003.*
Toungouz et al. Tolerance induction in clinical transplantation: the pending questions.□□Transplantation. 75(9 Suppl):58S–60S, 2003.*

(Continued)

Primary Examiner—Elizabeth C. Kemmerer
Assistant Examiner—Bridget E. Bunner
(74) Attorney, Agent, or Firm—Kathleen M. Williams; Elizabeth S. Spar; Palmer & Dodge LLP

(57) ABSTRACT

Methods and compositions are described for the treatment of type I insulin-dependent diabetes mellitus and other conditions using newly identified stem cells that are capable of differentiation into a variety of pancreatic islet cells, including insulin-producing beta cells, as well as hepatocytes. Nestin has been identified as a molecular marker for pancreatic stem cells, while cytokeratin-19 serves as a marker for a distinct class of islet ductal cells. Methods are described whereby nestin-positive stem cells can be isolated from pancreatic islets and cultured to obtain further stem cells or pseudo-islet like structures. Methods for ex vivo differentiation of the pancreatic stem cells are disclosed. Methods are described whereby pancreatic stem cells can be isolated, expanded, and transplanted into a patient in need thereof, either allogeneically, isogeneically or xenogenically, to provide replacement for lost or damaged insulin-secreting cells or other cells.

2 Claims, 18 Drawing Sheets

OTHER PUBLICATIONS

Mathew et al. Immunoregulatory role of chimerism in clinical organ transplantation. Bone Marrow Transplantation 28: 115–119, 2001.*

Mathew et al. Immune responses and their regulation by donor bone marrow cells in clinical organ transplantation. Transplant Immunol 11: 307–321, 2003.*

Monaco AP. Chimerism in organ transplantation: conflicting experiments and clinical observations.□□Transplantation. 75(9 Suppl):13S–16S, 2003.*

Kawai, T et al. Long–term islet allograft function in the absence of chronic immunosuppression a case report of a nonhuman primate previously made tolerant to a renal allograft from the same donor. Transplantation. 72(2):351–354, 2001.*

Exner, BG et al. Tolerance induction for islet transplantation. Ann Transplant. 2(3):77–80, 1997.*

Herve, P. Donor–derived hematopoietic stem cells in organ transplantation: technical aspects and hurdles yet to be cleared. Transplantation. 75(9 Suppl):55S–57S, 2003.*

Ikehara, S. New strategies for allogeneic bone marrow transplantation and organ allografts.□□Acta Haematol. 101(2):68–77, 1999.*

Lanza et al. Xenotransplantation of canine, bovine, and porcine islets in diabetic rats without immunosuppression. Proc Natl Acas Sci USA 88: 11100–11104, 1991.*

Abraham, EJ et al. Human pancreatic islet–derived progenitor cell engraftment in immunocompetent mice. Am J Pathol. 164(3):817–830, 2004.*

Bottino R et al. Pancreas and islet cell transplantation. Best Pract Res Clin Gastroenterol. 16(3):457–474, 2002.*

De Pauw, L et al. Infusion of donor–derived hematopoietic stem cells in organ transplantation: clinical data. Transplantation. 75(9 Suppl):46S–49S, 2003.* de Vries–van der Zwan et al. Stem cell transfusion as a new method for the induction of tolerance in organ transplantation. Transplantation Proceedings 29: 1209–1210, 1997.*

Peck, et al., Pancreatic stem cells: building blocks for a better surrogate islet to treat type 1 diabetes, 2001, *Ann Med.* 33: 186–192.

Zulewski, et al. Multipotential Nestin–Positive Stem Cells Isolated From Adult Pancreatic Islets Differentiate Ex Vivo Into Pancreatic Endocrine, Exocrine, and Hepatic Phenotypes, *Diabetes*, 50:521–533, 2001.

Zhou, et al., The ABC transporter Bcrpl/ABCG2 is expressed in a wide variety of stem cells and is a molecular determinant of the side–population phenotype, 2001, *Nature Medicine* vol. 7, No. 9: 1028–1034.

Bouwens, L., *Transdifferentiation Versus Stem Cell Hypothesis for the Regeneration of Islet Beta Cells in the Pancreas*, (1998), Micros. Res. Tech. 43:332–336.

Cornelius, J. et al., *In–Vitro Generation of Islets in Long–Term Cultures of Pluripotent Stem Cells from Adult Mouse Pancreas*. (1997), Horm. Metab. Res. 29:271–277.

Xu, G. et al. *Exendin–4 Stimulates Both Beta–Cell Replication and Neogenesis, Resulting in Increased Beta–Cell Mass and Improved Glucose Tolerance in Diabetic Rats*. (1999), Diabetes. 48:2270–2276.

Ramiya, V. et al. *Reversal of Insulin–Dependent Diabetes Using Islets Generated In–Vitro from Pancreatic Stem Cells*. (2000), Nature Medicine. 6:278–282.

Stoffers, D. et al. *Insulinotropic Glucagon–Like Peptide 1 Agonists Stimulate Expression of Homeodomain Protein IDX–1 and Increase Islet Size in Mouse Pancreas*. (2000), Diabetes. 49:741–748.

Ferber, S. et al. *Pancreatic and Duodenal Homeobox Gene 1 Induces Expression of Insulin Genes in Liver and Ameliorates Streptozotocin–Induced Hyperglycemia.* (2000), Nature Medicine. 6:568–572.

Lendahl, U. et al. *CNS Stem Cells Express a New Class of Intermediate Filament Protein.* (1990), Cell. 60:585–595.

Dahlstrand, J. et al. *Characterization of the Human Nestin Gene Reveals a Close Evolutionary Relationship to Neurofilaments*. (1992), Journal of Cell Science. 103:589–597.

Hunziker & Stein. *Nestin–Expressing Cells in the Pancreatic Islets of Langerhans*. (2000), Biochem. & Biophys. Res. Comm. 271:116–119.

Beattie, et al. *Acid β–Galactosidase: A Developmentally Regulated Marker of Endocrine Cell Precursors in the Human Fetal Pancreas*. (1994). Journ. of Clinical Endocrinology & Metab. 78(5):1232–1240.

Yasumizu, et al. *Treatment of type 1 Diabetes mellitus in Non–Obese Diabetic Mice by Transplantation of Allogeneic Bone Marrow and Pancreatic Tissue*. (1987), PNAS USA. 84:6555–6557.

* cited by examiner

FORWARD PRIMER [GCGGGGCGGTGCGTGACTAC]
REVERSE PRIMER [GGGTGGTGAGGGTTGAGGTTTGTG]

NESTIN POSITIVE CELLS PROLIFERATE AROUND ISLETS IN VITRO

100x

200x

Nestin Amino Acid Sequence:
"MEGCMGEESFQMWELNRRLEAYLGRVKALEEQNELLSAGLGGLR
RQSADTSWRAHADDELAALRALVDQRWREKHAAEVARDNLAEELEGVAGRCEQLRL
ARERTTEEVARNRRAVEAEKCARAWLSSQGAELERELEALRVAHEEERVGLNAQAAC
APRLPAPPRPPAPAPEVEELARRLGEAWRGAVRGYQERVAHMETSLDQTRERLARAVQ
GAR
EVRLELQQLQAERGGLLERRAALEQRLEGRWQERLRATEKFQLAVEALEQEKQGLQSQ
IAQVLEGRQQLAHLKMSLSLEVATYRTLLEAENSRLQTPGGGSKTSLSFQDPKLELQF
PRTPEGRRLGSLLPVLSPTSLPSPLPATLETPVPAFLKNQEFLQARTPTLASTPIPPT
PQAPSPAVDAEIRAQDAPLSLLQTQGGRKQAPEPLRAEARVAIPASVLPGPEEPGGQR
QEASTGQSPEDHASLAPPLSPDHSSLEAKDGESGGSRVFSICRGEGEGQIWGLVEKET
AIEGKVVSSLQQEIWEEEDLNRKEIQDSQVPLEKETLKSLGEEIQESLKTLENQSHET
LERENQECPRSLEEDLETLKSLEKENKRAIKGCGGSETSRKRGCRQLKPTGKEDTQTL
QSLQKENQELMKSLEGNLETFLFPGTENQELVSSLQENLESLTALEKENQEPLRSPEV
GDEEALRPLTKENQEPLRSLEDENKEAFRSLEKENQEPLKTLEEEDQSIVRPLETENH
KSLRSLEEQDQETLRTLEKETQQRRRSLGEQDQMTLRPPEKVDLEPLKSLDQEIARPL
ENENQEFLKSLKEESVEAVKSLETEILESLKSAGQENLETLKSPETQAPLWTPEEINK
SGGNESSRKGNSRTTGVCGSEPRDIQTPGRGESGIIEISGSMEPGEFEISRGVDKESQ
RNLEEEENLGKGEYQESLRSLEEEGQELPQSADVQRWEDTVEKDQELAQESPPGMAGV
ENKDEAELNLREQDGFTGKEEVVEQGELNATEEVWFPGEGHPENPEPKEQRGLVEGAS
VKGGAEGLQDPEGQSQQVGTPGLQAPQGLPEAIEPLVEDDVAPGGDQASPEVMLGSEP
AMGESAAGAEPGLGQGVGGLGDPGHLTREEVMEPPLEEESLEAKRVQGLEGPRKDLEE
AGGLGTEFSELPGKSRDPWEPPREGREESEAEAPRGAEEAFPAETLGHTGSDAPSWP
LGSEEAEEDVPPVLVSPSPTYTPILEDAPGLQPQAEGSQEASWGVVQGRAEAGKVESEQ
EELGSGEIPEGLQEEGEESREESEEDELGETLPDSTPLGFYLRSPTSPRWTPLESRGH
PLKETGKEGWDPAVLASEGLEEPSEKEEGEEGEEECGRDSDLSEEFEDLGTEAPFLPG
VPGEVAEPLGQVPQLLLDPAAWDRDGESDGFADEEESGEEGEEDQEEGREPGAGRWGP
GSSVGSLQALSSSQRGEFLESDSVSVSVPWDDSLRGAVAGAPKTALETESQDSAEPSG
SEEESDPVSLEREDKVPGPLEIPSGMEDAGPGADIIGVNGQGPNLEGKSQHVNGGVMN
GLEQSEESGARNALVSEGDRGSPFQEEEGSALKRSSAGAPVHLGQGQFLKFTQREGDR
ESWSSGED"

Nestin Nucleotide Sequence:
BASE COUNT 1238 a 1176 c 1676 g 764 t ORIGIN 1
atggagggct gcatgggggga ggagtcgttt cagatgtggg agctcaatcg gcgcctggag 61
gcctacctgg gccgggtcaa ggcgctggag gagcagaatg agctgctcag cgccggactc 121
gggggggctcc ggcgacaatc cgcggacacc tcctggcggg cgcatgccga cgacgagctg 181
gcggccctgc gtgcgctcgt tgaccaacgc tggcgggaga agcacgcggc cgaggtggcg 241
cgcgacaacc tggctgaaga gctggagggc gtggcaggcc gatgcgagca gctgcggctg 301
gcccgggagc ggacgacgga ggaggtagcc cgcaaccggc gcgccgtcga ggcagagaaa
361 tgcgcccggg cctggctgag tagccagggg gcagagctgg agcgcgagct agaggctcta
421 cgcgtggcgc acgaggagga gcgcgtcggt ctgaacgcgc aggctgcctg tgccccccgc

FIG. 7A

```
 481 ctgcccgcgc cgccccggcc tcccgcgccg gccccggagg tagaggagct ggcaaggcga
 541 ctgggcgagg cgtggcgcgg ggcagtgcgc ggctaccagg agcgcgtggc acacatggag
 601 acgtcgctgg accagacccg cgagcgcctg gcccgggcgg tgcagggtgc ccgcgaggtc
 661 cgcctggagc tgcagcagct ccaggctgag cgcggaggcc tcctggagcg cagggcagcg
 721 ttggaacaga ggttggaggg ccgctggcag gagcggctgc gggctactga aaagttccag
 781 ctggctgtgg aggccctgga gcaggagaaa cagggcctac agagccagat cgctcaggtc
 841 ctggaaggtc ggcagcagct ggcgcacctc aagatgtccc tcagcctgga ggtggccacg
 901 tacaggaccc tcctggaggc tgagaactcc cggctgcaaa cacctggcgg tggctccaag
 961 acttccctca gctttcagga ccccaagctg gagctgcaat tccctaggac cccagagggc
1021 cggcgtcttg gatctttgct cccagtcctg agcccaactt ccctcccctc acccttgcct
1081 gctacccttg agacacctgt gccagccttt cttaagaacc aagaattcct ccaggcccgt
1141 acccctacct tggccagcac ccccatcccc ccacacctc aggcaccctc tcctgctgta
1201 gatgcagaga tcagagccca ggatgctcct ctctctctgc tccagacaca gggtgggagg
1261 aaacaggctc cagagcccct gcgggctgaa gccagggtgg ccattcctgc cagcgtcctg
1321 cctggaccag aggagcctgg gggccagcgg caagaggcca gtacaggcca
gtccccagag 1381 gaccatgcct ccttggcacc acccctcagc cctgaccact ccagtttaga
ggctaaggat 1441 ggagaatccg gtgggtctag agtgttcagc atatgccgag gggaaggtga
agggcaaatc 1501 tgggggttgg tagagaaaga aacagccata gagggcaaag tggtaagcag
cttgcagcag 1561 gaaatatggg aagaagagga tctaaacagg aaggaaatcc aggactccca
ggttcctttg 1621 gaaaagaaa ccctgaagtc tctgggagag gagattcaag agtcactgaa
gactctggaa 1681 aaccagagcc atgagacact agaaagggag aatcaagaat gtccgaggtc
tttagaagaa 1741 gacttagaaa cactaaaaag tctagaaaag gaaaataaaa gagctattaa
aggatgtgga 1801 ggtagtgaga cctctagaaa aagaggctgt aggcaactta agcctacagg
aaaagaggac 1861 acacagacat tgcaatccct gcaaaaggag aatcaagaac taatgaaatc
tcttgaaggt 1921 aatctagaga catttttatt tccaggaacg gaaaatcaag aattagtaag
ttctctgcaa 1981 gagaacttag agtcattgac agctctggaa aaggagaatc aagagccact
gagatctcca 2041 gaagtagggg atgaggaggc actgagacct ctgacaaagg agaatcagga
acccctgagg 2101 tctcttgaag atgagaacaa agaggccttt agatctctag aaaaagagaa
ccaggagcca 2161 ctgaagactc tagaagaaga ggaccagagt attgtgagac ctctagaaac
agagaatcac 2221 aaatcactga ggtctttaga agaacaggac caagagacat tgagaactct
tgaaaaagag 2281 actcaacagc gacggaggtc tctaggggaa caggatcaga tgacattaag
accccagaa 2341 aaagtggatc tagaaccact gaagtctctt gaccaggaga tagctagacc
tcttgaaaat 2401 gagaatcaag agttcttaaa gtcactcaaa gaagagagcg tagaggcagt
aaaatcttta 2461 gaaacagaga tcctagaatc actgaagtct gcgggacaag agaacctgga
aacactgaaa 2521 tctccagaaa ctcaagcacc actgtggact ccagaagaaa taaataaatc
aggggggcaat 2581 gaatcctcta gaaaaggaaa ttcaagaacc actggagtct gtggaagtga
accaagagac 2641 attcagactc ctggaagagg agaatcagga atcattgaga tctctgggag
catggaacct 2701 ggagaatttg agatctccag aggagtagac aaggaaagtc aaaggaatct
ggaagaggaa 2761 gagaacctgg gaaagggaga gtaccaagag tcactgaggt ctctggagga
ggagggacag 2821 gagctgccgc agtctgcaga tgtgcagagg tgggaagata cggtggagaa
ggaccaagaa 2881 ctggctcagg aaagccctcc tgggatggct ggagtggaaa ataaggatga
ggcagagctg 2941 aatctaaggg agcaggatgg cttcactggg aaggaggagg tggtagagca
gggagagctg 3001 aatgccacag aggaggtctg gttcccaggc gaggggcacc
```

FIG. 7B cagagaaccc tgagcccaaa 3061 gagcagagag gcctggttga gggagccagt
gtgaagggag gggctgaggg cctccaggac 3121 cctgaagggc aatcacaaca
ggtggggacc ccaggcctcc aggctcccca ggggctgcca 3181 gaggcgatag agcccctggt
ggaagatgat gtggccccag ggggtgacca agcctcccca 3241 gaggtcatgt tggggtcaga
gcctgccatg ggtgagtctg ctgcgggagc tgagccaggc 3301 ctggggcagg gggtgggagg
gctgggggac ccaggccatc tgaccaggga agaggtgatg 3361 gaaccacccc
tgaagagga gagtttggag gcaaagaggg ttcagggctt ggaagggcct 3421 agaaaggacc
tagaggaggc aggtggtctg gggacagagt tctccgagct gcctgggaag 3481 agcagagacc
cttgggagcc tcccagggag ggtagggagg agtcagaggc tgaggccccc 3541
aggggagcag aggaggcgtt ccctgctgag accctgggcc acactggaag tgatgcccct 3601
tcaccttggc ctctggggtc agaggaagct gaggaggatg taccaccagt gctggtctcc 3661
cccagcccaa cgtacacccc gatcctggaa gatgcccctg ggctccagcc tcaggctgaa 3721
gggagtcagg aggctagctg gggggtgcag gggagggctg aagctgggaa agtagagagc 3781
gagcaggagg agttgggttc tggggagatc cccgagggcc tccaggagga aggggaggag 3841
agcagagaag agagcgagga ggatgagctc ggggagaccc ttccagactc cactcccctg 3901
ggcttctacc tcaggtcccc cacctccccc aggtggaccc cactggagag cagaggccac 3961
cccctcaagg agactggaaa ggagggctgg gatcctgctg tcctggcttc cgagggcctt 4021
gaggaaccct cagaaaagga ggaggggggag gagggagaag aggagtgtgg ccgtgactct
4081 gacctgtcag aagaatttga ggacctgggg actgaggcac ctttcttcc tggggtccct
4141 ggggaggtgg cagaacctct gggccaggtg cccagctgc tactggatcc tgcagcctgg
4201 gatcgagatg gggagtctga tgggttgca gatgaggaag aaagtggggga ggagggagag
4261 gaggatcagg aggaggggag ggagccaggg gctgggcggt ggggccagg gtcttctgtt
4321 ggcagcctcc aggccctgag tagctcccag agaggggaat tcctggagtc tgattctgta
4381 agtgtcagcg tcccctggga tgacagcttg aggggtgcag tggctggtgc ccccaagact
4441 gccctggaaa cggagtccca ggacagtgct gagccttctg gctcagagga agagtctgac
4501 cctgttttcct tggagaggga ggacaaagtc cctggccctc tagagatccc cagtgggatg
4561 gaggatgcag gcccagggc agacatcatt ggtgttaatg gccagggtcc caacttggag
4621 gggaagtcac agcatgtaaa tgggggagta atgaacgggc tggagcagtc tgaggaaagt
4681 ggggcaagga atgcgctagt ctctgaggga gaccgaggga gccctttca ggaggaggag
4741 gggagtgctc tgaagaggtc ttcggcaggg gctcctgttc acctgggcca gggtcagttc
4801 ctgaagttca ctcagaggga aggagataga gagtcctggt cctcaggga ggac //

FIG. 7C

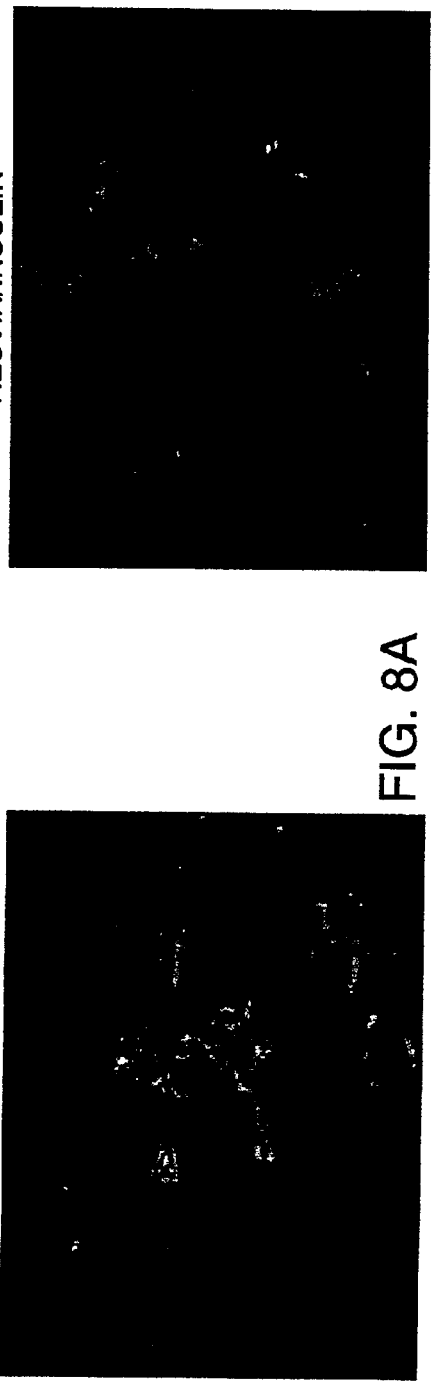
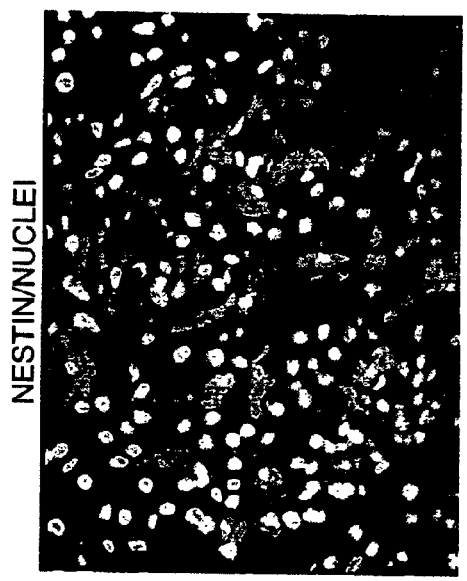
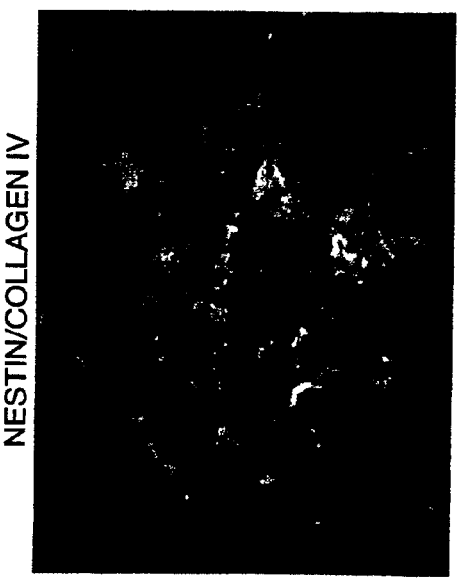
FIG. 8A NESTIN/INSULIN E16
FIG. 8B NESTIN/INSULIN P60
FIG. 8C NESTIN/COLLAGEN IV P60
FIG. 8D NESTIN/NUCLEI P60

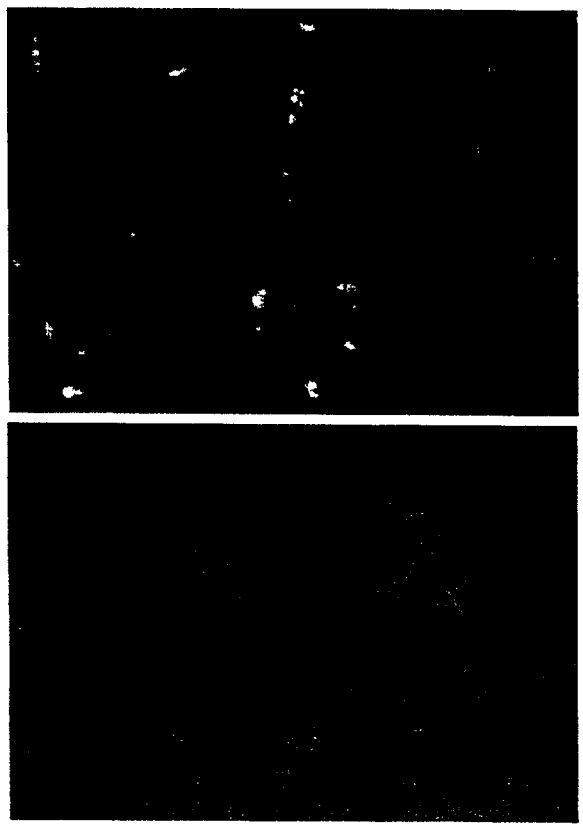
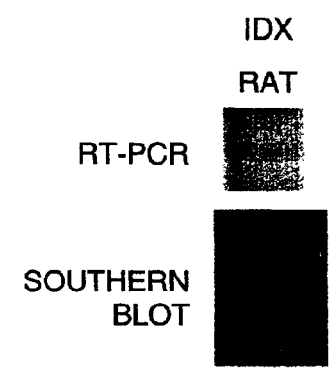
FIG. 10B
FIG. 10A
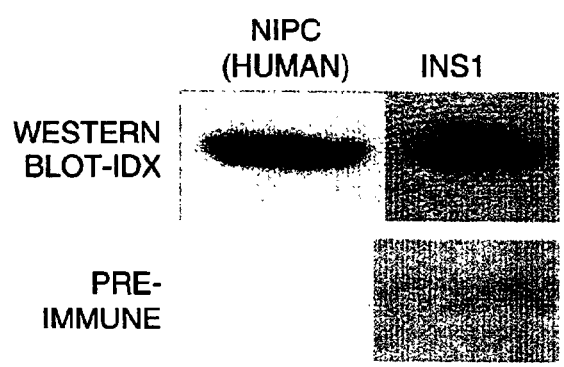
FIG. 10C
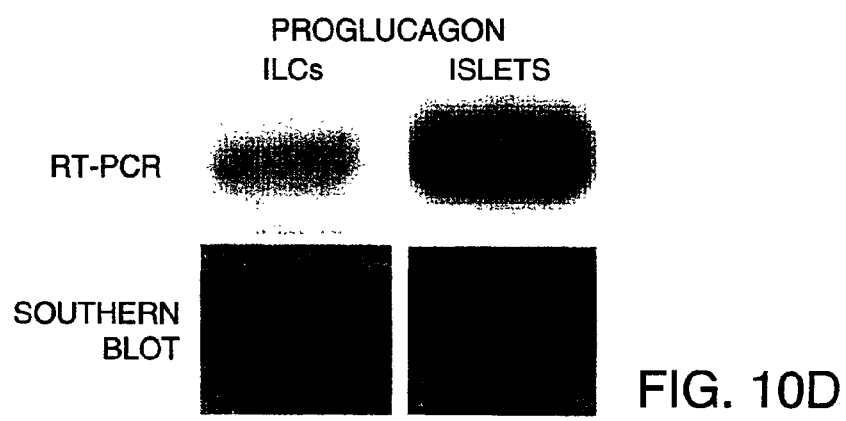
FIG. 10D

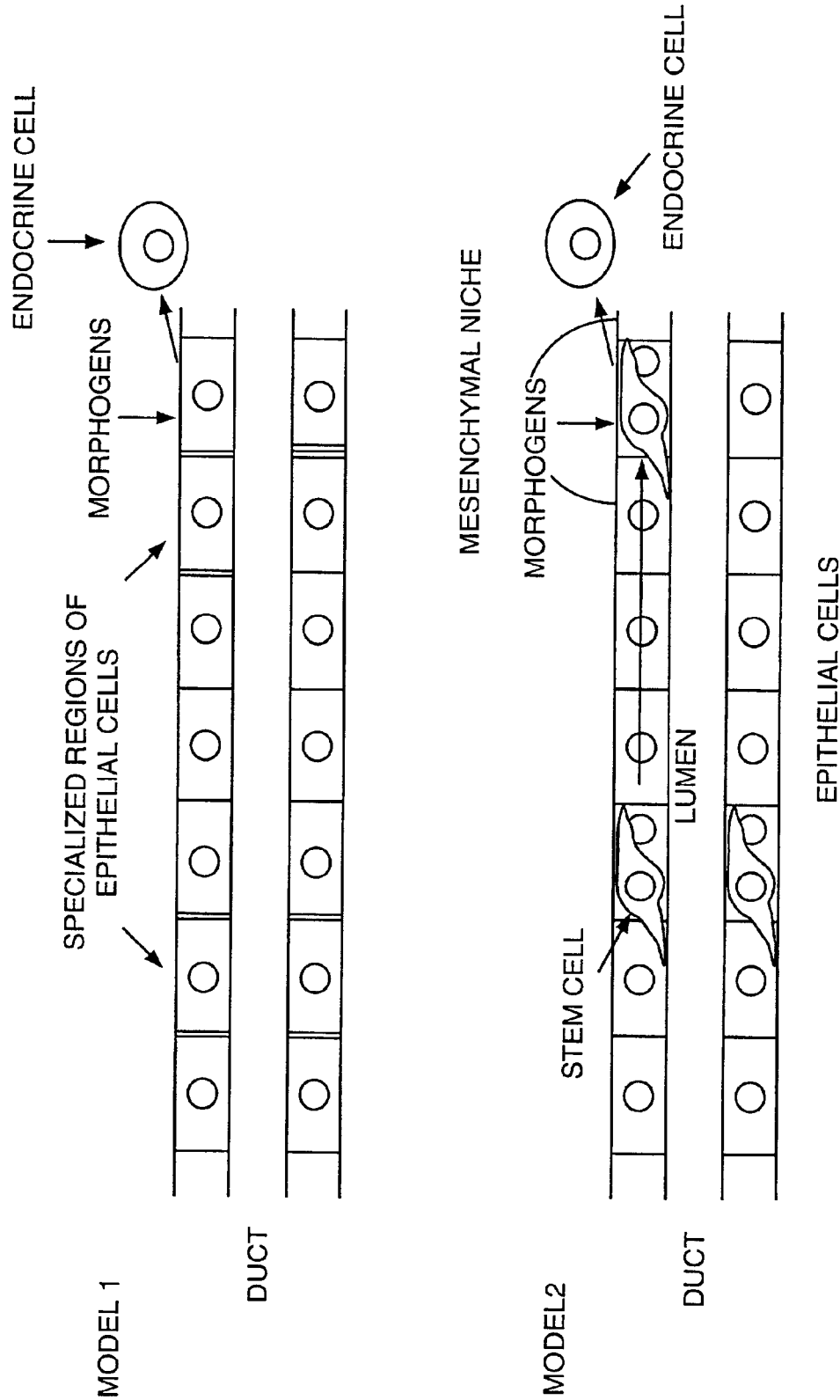

SEQUENCE LISTING

<160> NUMBER OF SEQ ID NOS: 55

<210> SEQ ID NO 1
<211> LENGTH: 4854
<212> TYPE: DNA
<213> ORGANISM: Homo sapiens

<400> SEQUENCE: 1

```
atggagggct gcatggggga ggagtcgttt cagatgtggg agctcaatcg gcgcctggag    60
```

```
gcctacctgg gccgggtcaa ggcgctggag gagcagaatg agctgctcag cgccggactc    120
gggggggctcc ggcgacaatc cgcggacacc tcctggcggg cgcatgccga cgacgagctg   180
gcggccctgc gtgcgctcgt tgaccaacgc tggcgggaga agcacgcggc cgaggtggcg    240
cgcgacaacc tggctgaaga gctggagggc gtggcaggcc gatgcgagca gctgcggctg    300
gcccgggagc ggacgacgga ggaggtagcc cgcaaccggc gcgccgtcga ggcagagaaa    360
tgcgcccggg cctggctgag tagccagggg gcagagctgg agcgcgagct agaggctcta    420
cgcgtggcgc acgaggagga gcgcgtcggt ctgaacgcgc aggctgcctg tgcccccgc     480
ctgcccgcgc cgccccggcc tcccgcgccg gccccggagg tagaggagct ggcaaggcga    540
ctgggcgagg cgtggcgcgg ggcagtgcgc ggctaccagg agcgcgtggc acacatggag    600
acgtcgctgg accagacccg cgagcgcctg gcccgggcgg tgcagggtgc ccgcgaggtc    660
cgcctgagc tgcagcagct ccaggctgag cgcggaggcc tcctggagcg cagggcagcg    720
ttggaacaga ggttggaggg ccgctggcag gagcggctgc gggctactga aaagttccag    780
ctggctgtgg aggccctgga gcaggagaaa cagggcctac agagccagat cgctcaggtc    840
ctggaaggtc ggcagcagct ggcgcacctc aagatgtccc tcagcctgga ggtggccacg    900
tacaggaccc tcctggaggc tgagaactcc cggctgcaaa cacctggcgg tggctccaag    960
acttccctca gctttcagga ccccaagctg agctgcaat tccctaggac cccagagggc   1020
cggcgtcttg gatctttgct cccagtcctg agcccaactt ccctcccctc acccttgcct   1080
gctacccttg agacacctgt gccagccttt cttaagaacc aagaattcct ccaggcccgt   1140
accccctacct tggccagcac ccccatcccc cccacacctc aggcaccctc tcctgctgta   1200
gatgcagaga tcagagccca ggatgctcct ctctctctgc tccagacaca gggtggggag   1260
aaacaggctc cagagcccct gcgggctgaa gccagggtgg ccattcctgc cagcgtcctg   1320
cctggaccag aggagcctgg gggccagcgg caagaggcca gtacaggcca gtccccagag   1380
gaccatgcct ccttggcacc accccctcagc cctgaccact ccagtttaga ggctaaggat   1440
ggagaatccg gtgggtctag agtgttcagc atatgccgag gggaaggtga agggcaaatc   1500
tgggggttgg tagagaaaga aacagccata gagggcaaag tggtaagcag cttgcagcag   1560
gaaatatggg aagaagagga tctaaacagg aaggaaatcc aggactccca ggttcctttg   1620
gaaaaagaaa ccctgaagtc tctgggagag gagattcaag agtcactgaa gactctggaa   1680
aaccagagcc atgagacact agaaagggag aatcaagaat gtccgaggtc tttagaagaa   1740
gacttagaaa cactaaaaag tctagaaaag gaaaataaaa gagctattaa aggatgtgga   1800
ggtagtgaga cctctagaaa aagaggctgt aggcaactta agcctacagg aaaagaggac   1860
acacagacat tgcaatccct gcaaaaggag aatcaagaac taatgaaatc tcttgaaggt   1920
aatctagaga catttttatt tccaggaacg gaaaatcaag aattagtaag ttctctgcaa   1980
gagaacttag agtcattgac agctctggaa aaggagaatc aagagccact gagatctcca   2040
gaagtagggg atgaggaggc actgagacct ctgacaaagg agaatcagga acccctgagg   2100
tctcttgaag atgagaacaa agaggccttt agatctctag aaaagagaa ccaggagcca    2160
ctgaagactc tagaagaaga ggaccagagt attgtgagac ctctagaaac agagaatcac   2220
aaatcactga ggtctttaga agaacaggac caagagacat tgagaactct tgaaaagag   2280
actcaacagc gacggaggtc tctaggggaa caggatcaga tgacattaag accccccagaa  2340
aaagtggatc tagaaccact gaagtctctt gaccaggaga tagctagacc tcttgaaaat   2400
```

```
gagaatcaag agttcttaaa gtcactcaaa gaagagagcg tagaggcagt aaaatcttta    2460
gaaacagaga tcctagaatc actgaagtct gcgggacaag agaacctgga aacactgaaa    2520
tctccagaaa ctcaagcacc actgtggact ccagaagaaa taaataaatc aggggcaat     2580 gaatcctcta gaaaggaaa ttcaagaacc actggagtct gtggaagtga accaagagac     2640
attcagactc ctggaagagg agaatcagga atcattgaga tctctgggag catggaacct    2700
ggagaatttg agatctccag aggagtagac aaggaaagtc aaaggaatct ggaagaggaa    2760
gagaacctgg gaaagggaga gtaccaagag tcactgaggt ctctggagga gagggacag    2820 gagctgccgc agtctgcaga tgtgcagagg tgggaagata cggtggagaa ggaccaagaa    2880
ctggctcagg aaagccctcc tgggatggct ggagtggaaa ataaggatga ggcagagctg    2940
aatctaaggg agcaggatgg cttcactggg aaggaggagg tggtagagca gggagagctg    3000
aatgccacag aggaggtctg gttcccaggc gaggggcacc cagagaaccc tgagcccaaa    3060
gagcagagag gcctggttga gggagccagt gtgaagggag gggctgaggg cctccaggac    3120
cctgaagggc aatcacaaca ggtggggacc ccaggcctcc aggctcccca ggggctgcca    3180
gaggcgatag agcccctggt ggaagatgat gtggccccag gggtgacca agcctcccca     3240 gaggtcatgt tgggtcaga gcctgccatg ggtgagtctg ctgcgggagc tgagccaggc     3300
ctggggcagg ggtgggagg gctgggggac ccaggccatc tgaccaggga agaggtgatg     3360
gaaccacccc tggaagagga gagtttggag gcaaagaggg ttcagggctt ggaagggcct    3420
agaaaggacc tagaggaggc aggtggtctg gggacagagt tctccgagct gcctgggaag    3480
agcagagacc cttgggagcc tcccagggag ggtagggagg agtcagaggc tgaggccccc    3540
aggggagcag aggaggcgtt ccctgctgag accctgggcc acactggaag tgatgcccct    3600
tcaccttggc ctctggggtc agaggaagct gaggaggatg taccaccagt gctggtctcc    3660
cccagcccaa cgtacacccc gatcctggaa gatgcccctg gctccagcc tcaggctgaa    3720 gggagtcagg aggctagctg ggggtgcag gggagggctg aagctgggaa agtagagagc    3780
gagcaggagg agttgggttc tggggagatc cccgagggcc tccaggagga aggggaggag    3840
agcagagaag agagcgagga ggatgagctc ggggagaccc ttccagactc cactcccctg    3900
ggcttctacc tcaggtcccc cacctccccc aggtggaccc cactggagag cagaggccac    3960
cccctcaagg agactggaaa ggagggctgg gatcctgctg tcctggcttc cgagggcctt    4020
gaggaaccct cagaaaagga ggaggggag gaggagaag aggagtgtgg ccgtgactct      4080
gacctgtcag aagaatttga ggacctgggg actgaggcac cttttcttcc tggggtccct    4140
ggggaggtgg cagaacctct ggccaggtg ccccagctgc tactggatcc tgcagcctgg    4200
gatcgagatg gggagtctga tgggtttgca gatgaggaag aaagtgggga ggaggagag    4260 gaggatcagg aggaggggag ggagccaggg gctggcggt ggggccagg gtcttctgtt     4320 ggcagcctcc aggccctgag tagctcccag agagggaat tcctgagtc tgattctgta    4380 agtgtcagcg tcccctggga tgacagcttg aggggtgcag tggctggtgc ccccaagact   4440
gccctggaaa cggagtccca ggacagtgct gagccttctg gctcagagga agagtctgac   4500 cctgttttcct tggagaggga ggacaaagtc cctggccctc tagagatccc cagtgggatg   4560
gaggatgcag gccaggggc agacatcatt ggtgttaatg ccagggtcc caacttggag     4620 gggaagtcac agcatgtaaa tgggggagta atgaacgggc tggagcagtc tgaggaaagt   4680
ggggcaagga atgcgctagt ctctgaggga gaccgaggga gccccttcca ggaggaggag   4740
gggagtgctc tgaagaggtc ttcggcaggg gctcctgttc acctgggcca gggtcagttc   4800
```

-continued ctgaagttca ctcagaggga aggagataga gagtcctggt cctcagggga ggac    4854

<210> SEQ ID NO 2
<211> LENGTH: 1618
<212> TYPE: PRT
<213> ORGANISM: Homo sapiens

<400> SEQUENCE: 2

Met Glu Gly Cys Met Gly Glu Glu Ser Phe Gln Met Trp Glu Leu Asn
1               5                   10                  15

Arg Arg Leu Glu Ala Tyr Leu Gly Arg Val Lys Ala Leu Glu Glu Gln
            20                  25                  30

Asn Glu Leu Leu Ser Ala Gly Leu Gly Gly Leu Arg Arg Gln Ser Ala
        35                  40                  45

Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Glu Leu Glu Gly Val Ala Gly Arg Cys Glu
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Gly Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Leu Pro Ala Pro Pro Arg Pro Pro Ala Pro Ala Pro Glu Val Glu Glu
                165                 170                 175

Leu Ala Arg Arg Leu Gly Glu Ala Trp Arg Gly Ala Val Arg Gly Tyr
            180                 185                 190

Gln Glu Arg Val Ala His Met Glu Thr Ser Leu Asp Gln Thr Arg Glu
        195                 200                 205

Arg Leu Ala Arg Ala Val Gln Gly Ala Arg Glu Val Arg Leu Glu Leu
    210                 215                 220

Gln Gln Leu Gln Ala Glu Arg Gly Gly Leu Leu Glu Arg Arg Ala Ala
225                 230                 235                 240

Leu Glu Gln Arg Leu Glu Gly Arg Trp Gln Glu Arg Leu Arg Ala Thr
                245                 250                 255

Glu Lys Phe Gln Leu Ala Val Glu Ala Leu Glu Gln Glu Lys Gln Gly
            260                 265                 270

Leu Gln Ser Gln Ile Ala Gln Val Leu Glu Gly Arg Gln Gln Leu Ala
        275                 280                 285

His Leu Lys Met Ser Leu Ser Leu Glu Val Ala Thr Tyr Arg Thr Leu
    290                 295                 300

Leu Glu Ala Glu Asn Ser Arg Leu Gln Thr Pro Gly Gly Gly Ser Lys
305                 310                 315                 320

Thr Ser Leu Ser Phe Gln Asp Pro Lys Leu Glu Leu Gln Phe Pro Arg
                325                 330                 335

Thr Pro Glu Gly Arg Arg Leu Gly Ser Leu Leu Pro Val Leu Ser Pro
            340                 345                 350

Thr Ser Leu Pro Ser Pro Leu Pro Ala Thr Leu Glu Thr Pro Val Pro
        355                 360                 365

-continued

```
Ala Phe Leu Lys Asn Gln Glu Phe Leu Gln Ala Arg Thr Pro Thr Leu
    370                 375                 380

Ala Ser Thr Pro Ile Pro Pro Thr Pro Gln Ala Pro Ser Pro Ala Val
385                 390                 395                 400

Asp Ala Glu Ile Arg Ala Gln Asp Ala Pro Leu Ser Leu Leu Gln Thr
                405                 410                 415

Gln Gly Gly Arg Lys Gln Ala Pro Glu Pro Leu Arg Ala Glu Ala Arg
            420                 425                 430

Val Ala Ile Pro Ala Ser Val Leu Pro Gly Pro Glu Glu Pro Gly Gly
        435                 440                 445

Gln Arg Gln Glu Ala Ser Thr Gly Gln Ser Pro Glu Asp His Ala Ser
    450                 455                 460

Leu Ala Pro Pro Leu Ser Pro Asp His Ser Ser Leu Glu Ala Lys Asp
465                 470                 475                 480

Gly Glu Ser Gly Gly Ser Arg Val Phe Ser Ile Cys Arg Gly Glu Gly
                485                 490                 495

Glu Gly Gln Ile Trp Gly Leu Val Glu Lys Glu Thr Ala Ile Glu Gly
            500                 505                 510

Lys Val Val Ser Ser Leu Gln Gln Glu Ile Trp Glu Glu Asp Leu
        515                 520                 525

Asn Arg Lys Glu Ile Gln Asp Ser Gln Val Pro Leu Glu Lys Glu Thr
    530                 535                 540

Leu Lys Ser Leu Gly Glu Glu Ile Gln Glu Ser Leu Lys Thr Leu Glu
545                 550                 555                 560

Asn Gln Ser His Glu Thr Leu Glu Arg Glu Asn Gln Glu Cys Pro Arg
                565                 570                 575

Ser Leu Glu Glu Asp Leu Glu Thr Leu Lys Ser Leu Glu Lys Glu Asn
            580                 585                 590

Lys Arg Ala Ile Lys Gly Cys Gly Gly Ser Glu Thr Ser Arg Lys Arg
        595                 600                 605

Gly Cys Arg Gln Leu Lys Pro Thr Gly Lys Glu Asp Thr Gln Thr Leu
    610                 615                 620

Gln Ser Leu Gln Lys Glu Asn Gln Glu Leu Met Lys Ser Leu Glu Gly
625                 630                 635                 640

Asn Leu Glu Thr Phe Leu Phe Pro Gly Thr Glu Asn Gln Glu Leu Val
                645                 650                 655

Ser Ser Leu Gln Glu Asn Leu Glu Ser Leu Thr Ala Leu Glu Lys Glu
            660                 665                 670

Asn Gln Glu Pro Leu Arg Ser Pro Glu Val Gly Asp Glu Glu Ala Leu
        675                 680                 685

Arg Pro Leu Thr Lys Glu Asn Gln Glu Pro Leu Arg Ser Leu Glu Asp
    690                 695                 700

Glu Asn Lys Glu Ala Phe Arg Ser Leu Glu Lys Glu Asn Gln Glu Pro
705                 710                 715                 720

Leu Lys Thr Leu Glu Glu Glu Asp Gln Ser Ile Val Arg Pro Leu Glu
                725                 730                 735

Thr Glu Asn His Lys Ser Leu Arg Ser Leu Glu Glu Gln Asp Gln Glu
            740                 745                 750

Thr Leu Arg Thr Leu Glu Lys Glu Thr Gln Gln Arg Arg Ser Leu
    755                 760                 765

Gly Glu Gln Asp Gln Met Thr Leu Arg Pro Pro Glu Lys Val Asp Leu
770                 775                 780
```

```
Glu Pro Leu Lys Ser Leu Asp Gln Glu Ile Ala Arg Pro Leu Glu Asn
785                 790                 795                 800

Glu Asn Gln Glu Phe Leu Lys Ser Leu Lys Glu Ser Val Glu Ala
            805                 810                 815

Val Lys Ser Leu Glu Thr Glu Ile Leu Glu Ser Leu Lys Ser Ala Gly
            820                 825                 830

Gln Glu Asn Leu Glu Thr Leu Lys Ser Pro Glu Thr Gln Ala Pro Leu
            835                 840                 845

Trp Thr Pro Glu Glu Ile Asn Lys Ser Gly Gly Asn Glu Ser Ser Arg
850                 855                 860

Lys Gly Asn Ser Arg Thr Thr Gly Val Cys Gly Ser Glu Pro Arg Asp
865                 870                 875                 880

Ile Gln Thr Pro Gly Arg Gly Glu Ser Gly Ile Ile Glu Ile Ser Gly
                885                 890                 895

Ser Met Glu Pro Gly Glu Phe Glu Ile Ser Arg Gly Val Asp Lys Glu
                900                 905                 910

Ser Gln Arg Asn Leu Glu Glu Glu Asn Leu Gly Lys Gly Glu Tyr
            915                 920                 925

Gln Glu Ser Leu Arg Ser Leu Glu Glu Glu Gly Gln Glu Leu Pro Gln
930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Lys Asp
            965                 970                 975

Glu Ala Glu Leu Asn Leu Arg Glu Gln Asp Gly Phe Thr Gly Lys Glu
            980                 985                 990

Glu Val Val Glu Gln Gly Glu Leu Asn Ala Thr Glu Glu Val Trp Phe
            995                1000                1005

Pro Gly Glu Gly His Pro Glu Asn Pro Glu Pro Lys Glu Gln Arg
    1010                1015                1020

Gly Leu Val Glu Gly Ala Ser Val Lys Gly Gly Ala Glu Gly Leu
    1025                1030                1035

Gln Asp Pro Glu Gly Gln Ser Gln Gln Val Gly Thr Pro Gly Leu
    1040                1045                1050

Gln Ala Pro Gln Gly Leu Pro Glu Ala Ile Glu Pro Leu Val Glu
    1055                1060                1065

Asp Asp Val Ala Pro Gly Gly Asp Gln Ala Ser Pro Glu Val Met
    1070                1075                1080

Leu Gly Ser Glu Pro Ala Met Gly Glu Ser Ala Ala Gly Ala Glu
    1085                1090                1095

Pro Gly Leu Gly Gln Gly Val Gly Gly Leu Gly Asp Pro Gly His
    1100                1105                1110

Leu Thr Arg Glu Glu Val Met Glu Pro Pro Leu Glu Glu Ser
    1115                1120                1125

Leu Glu Ala Lys Arg Val Gln Gly Leu Glu Gly Pro Arg Lys Asp
    1130                1135                1140

Leu Glu Glu Ala Gly Gly Leu Gly Thr Glu Phe Ser Glu Leu Pro
    1145                1150                1155

Gly Lys Ser Arg Asp Pro Trp Glu Pro Pro Arg Glu Gly Arg Glu
    1160                1165                1170

Glu Ser Glu Ala Glu Ala Pro Arg Gly Ala Glu Glu Ala Phe Pro
    1175                1180                1185

Ala Glu Thr Leu Gly His Thr Gly Ser Asp Ala Pro Ser Pro Trp
```

-continued

|     |     |     |
| --- | --- | --- |
| 1190 | 1195 | 1200 |

Pro Leu Gly Ser Glu Glu Ala Glu Glu Asp Val Pro Pro Val Leu
    1205                1210                1215

Val Ser Pro Ser Pro Thr Tyr Thr Pro Ile Leu Glu Asp Ala Pro
    1220                1225                1230

Gly Leu Gln Pro Gln Ala Glu Gly Ser Gln Ala Ser Trp Gly
    1235                1240                1245

Val Gln Gly Arg Ala Glu Ala Gly Lys Val Glu Ser Glu Gln Glu
    1250                1255                1260

Glu Leu Gly Ser Gly Glu Ile Pro Glu Gly Leu Gln Glu Glu Gly
    1265                1270                1275

Glu Glu Ser Arg Glu Glu Ser Glu Glu Asp Glu Leu Gly Glu Thr
    1280                1285                1290

Leu Pro Asp Ser Thr Pro Leu Gly Phe Tyr Leu Arg Ser Pro Thr
    1295                1300                1305

Ser Pro Arg Trp Thr Pro Leu Glu Ser Arg Gly His Pro Leu Lys
    1310                1315                1320

Glu Thr Gly Lys Glu Gly Trp Asp Pro Ala Val Leu Ala Ser Glu
    1325                1330                1335

Gly Leu Glu Glu Pro Ser Glu Lys Glu Glu Gly Glu Glu Gly Glu
    1340                1345                1350

Glu Glu Cys Gly Arg Asp Ser Asp Leu Ser Glu Glu Phe Glu Asp
    1355                1360                1365

Leu Gly Thr Glu Ala Pro Phe Leu Pro Gly Val Pro Gly Glu Val
    1370                1375                1380

Ala Glu Pro Leu Gly Gln Val Pro Gln Leu Leu Leu Asp Pro Ala
    1385                1390                1395

Ala Trp Asp Arg Asp Gly Glu Ser Asp Gly Phe Ala Asp Glu Glu
    1400                1405                1410

Glu Ser Gly Glu Glu Gly Glu Glu Asp Gln Glu Glu Gly Arg Glu
    1415                1420                1425

Pro Gly Ala Gly Arg Trp Gly Pro Gly Ser Ser Val Gly Ser Leu
    1430                1435                1440

Gln Ala Leu Ser Ser Ser Gln Arg Gly Glu Phe Leu Glu Ser Asp
    1445                1450                1455

Ser Val Ser Val Ser Val Pro Trp Asp Asp Ser Leu Arg Gly Ala
    1460                1465                1470

Val Ala Gly Ala Pro Lys Thr Ala Leu Glu Thr Glu Ser Gln Asp
    1475                1480                1485

Ser Ala Glu Pro Ser Gly Ser Glu Glu Glu Ser Asp Pro Val Ser
    1490                1495                1500

Leu Glu Arg Glu Asp Lys Val Pro Gly Pro Leu Glu Ile Pro Ser
    1505                1510                1515

Gly Met Glu Asp Ala Gly Pro Gly Ala Asp Ile Ile Gly Val Asn
    1520                1525                1530

Gly Gln Gly Pro Asn Leu Glu Gly Lys Ser Gln His Val Asn Gly
    1535                1540                1545

Gly Val Met Asn Gly Leu Glu Gln Ser Glu Glu Ser Gly Ala Arg
    1550                1555                1560

Asn Ala Leu Val Ser Glu Gly Asp Arg Gly Ser Pro Phe Gln Glu
    1565                1570                1575

Glu Glu Gly Ser Ala Leu Lys Arg Ser Ser Ala Gly Ala Pro Val
    1580                1585                1590

```
His Leu Gly Gln Gly Gln Phe Leu Lys Phe Thr Gln Arg Glu Gly
    1595            1600                1605

Asp Arg Glu Ser Trp Ser Ser Gly Glu Asp
    1610            1615
```

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcggggcggt gcgtgactac                                              20

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
aggcaagggg gaagagaagg atgt                                         24

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
aagctgaagc cgaatttcct tgggatacca gagga                             35

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
acagccagta cttcaagacc                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ctgtgtcagc acgcacgtta                                              20

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
tggattccac accaggcatt gaccatgcca                                   30
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
cagcgttgga gagtccaaat                                           20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ttaaactcct gtggggttgg                                           20

<210> SEQ ID NO 11
<211> LENGTH: 37
<212> TYPE: DNA
<213> ORGANISM: Artificial Sequence
<220> FEATURE:
<223> OTHER INFORMATION: Primer

<400> SEQUENCE: 11
aaaccagcag cggatctcag tggtgtggaa cgatgat                        37

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
atcactggag cagggaagt                                            19

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gctactacgt ttctttatct                                           19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
gcgtggaaaa gccagtggg                                            19

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15 agagggaat tcctggag                                          18

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ctgaggacca ggactctcta                                       20

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
tatgaacggg ctggagcagt ctgaggaaag t                           31

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cttttcgcgc gcccagcatt                                       20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
gatcttcctg tccctcgagc                                       20

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
aaccatgagg aggaaatcag tacgctgagg                            30

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
atctggactc caggcgtgcc                                       20

<210> SEQ ID NO 22

```
<211> LENGTH: 20
<212> TYPE: DNA
<213> ORGANISM: Artificial Sequence
<220> FEATURE:
<223> OTHER INFORMATION: Primer

<400> SEQUENCE: 22
agcaatgaat tccttggcag                                               20

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
cacgatgaat ttgagagaca tgctgaaggg                                    30

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
agaacagcac gtacacagcc                                               20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cctccgaaga aacagcaaga                                               20

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
tctcccttca cagcagaact aacacacggg                                    30

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
gcagtcctgc catcaatgtg                                               20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
```
gttggctgtg aataccacct                    20

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
ctggagagct gcatgggctc acaactgagg          30

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
gactttccag cagtcccata                     20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
gtttacttcc tgcagggaac                     20

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
ttgcactgga gaaggattac gtggcgttct a        31

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
tgaaggcgag aaggtgttcc                     20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ttcgagatac aggcagatat                     20

<210> SEQ ID NO 35
<211> LENGTH: 30
<212> TYPE: DNA

```
<213> ORGANISM: Artificial Sequence
<220> FEATURE:
<223> OTHER INFORMATION: Primer

<400> SEQUENCE: 35
agttagactt ttatgtcctg cctgtgctca                                          30

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cttcaggctg caccaagtgt                                                     20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gttgaccata gtcaggctgg                                                     20

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
gtcagatgtg aagatggcca cagacccaga                                          30

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gcatcaaatg tcagccctgg                                                     20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
caacgctgac atggaattcc                                                     20

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
tcgaggtctc atggatcata cagaatcagg                                          30
```

```
<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
caatgtgaga tgtctccagc                                                    20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
ccttgtagat tgcaggcaga                                                    20

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
ggactcccat ccagtgtctc cagaagtgat                                         30

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gagtagcagc tcagactgcc                                                    20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gtagacctct gggagctcct                                                    20

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
cgcagcactc agactacgtg cacctctgca                                         30

<210> SEQ ID NO 48
<211> LENGTH: 20
<212> TYPE: DNA
<213> ORGANISM: Artificial Sequence
<220> FEATURE:
```

```
<223> OTHER INFORMATION: Primer

<400> SEQUENCE: 48
gcagctgctc aactaatcac                                              20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
tcagcagcac aagtcccact                                              20

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
acgggcattc ttattagtca gattattggt                                   30

<210> SEQ ID NO 51
<211> LENGTH: 16
<212> TYPE: DNA
<213> ORGANISM: Artificial Sequence
<220> FEATURE:
<223> OTHER INFORMATION: Primer

<400> SEQUENCE: 51
aggcttcttc tacaca                                                  16

<210> SEQ ID NO 52
<211> LENGTH: 16
<212> TYPE: DNA
<213> ORGANISM: Artificial Sequence
<220> FEATURE:
<223> OTHER INFORMATION: Primer

<400> SEQUENCE: 52
caggctgcct gcacca                                                  16

<210> SEQ ID NO 53
<211> LENGTH: 16
<212> TYPE: DNA
<213> ORGANISM: Artificial Sequence
<220> FEATURE:
<223> OTHER INFORMATION: Primer

<400> SEQUENCE: 53
aggcagagga cctgca                                                  16

<210> SEQ ID NO 54
<211> LENGTH: 10
<212> TYPE: PRT
<213> ORGANISM: Artificial Sequence
<220> FEATURE:
<223> OTHER INFORMATION: Primer

<400> SEQUENCE: 54

Cys Phe Ile Ala Trp Leu Val Lys Gly Arg
1               5                   10
```

```
<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
gggtggtgag ggttgaggtt tgtg                                          24
```

METHOD OF PRE-INDUCING A STATE OF IMMUNE TOLERANCE BEFORE ORGAN TRANSPLANTATION

PRIORITY

The present application is a continuation in part application of U.S. application Ser. No. 09/731,255, filed Dec. 6, 2000, and claims priority to U.S. Application Ser. No. 60/169,082, filed Dec. 6, 1999, U.S. Application Ser. No. 60/215,109, filed Jun. 28, 2000, and U.S. Application Ser. No. 60/238,880, filed Oct. 6, 2000.

The invention was made at least in part using U.S. government funds, grants DK30457 and DK30834 awarded by the National Institutes of Health, and therefore the U.S. government may retain certain rights in the invention.

TECHNICAL FIELD OF THE INVENTION

The invention is related to the field of stem cells and their differentiation. In particular, it is related to the field of beta cells of the islets of Langerhans in the pancreas and nestin positive liver stem cells and their differentiation from stem cells or progenitor cells, and the use of pancreatic stem cells, progenitor cells, and differentiated beta cells or nestin positive liver stem cells or progenitor cells in transplantation.

BACKGROUND OF THE INVENTION

The origin of pancreatic islet cells, both during embryonic development and in a mature mammal, has remained uncertain despite intensive study. Certain ductal epithelial cells are capable of either differentiation or transdifferentiation to form beta cells and other cell types found in mature islets (Bouwens, 1998). Ductal cells from isolated islets can proliferate in culture and, if transplanted into an animal, can differentiate into functional beta cells (Cornelius et al., 1997).

It has been demonstrated that exendin-4, a long acting GLP-1 agonist, stimulates both the differentiation of β-cells from ductal progenitor cells (neogenesis) and proliferation of β-cells when administered to rats. In a partial pancreatectomy rat model of type 2 diabetes, the daily administration of exendin-4 for 10 days post pancreatectomy attenuated the development of diabetes. It has also been demonstrated that exendin-4 stimulates the regeneration of the pancreas and expansion of β-cell mass by neogenesis and proliferation of β-cells (Xu et al., 1999, Diabetes, 48:2270–2276).

Ramiya et al. have demonstrated that islets generated in vitro from pluripotent stem cells isolated from the pancreatic ducts of adult prediabetic non-obese diabetic (NOD) mice differentiate to form glucose responsive islets that can reverse insulin-dependent diabetes after being implanted, with or without encapsulation, into diabetic NOD mice (Ramiya et al., 2000, Nature Med., 6:278–282).

The insulinotropic hormone glucagon-like peptide (GLP)-1 which is produced by the intestine, enhances the pancreatic expression of the homeodomain transcription factor IDX-1 that is critical for pancreas development and the transcriptional regulation of the insulin gene. Concomitantly, GLP-1 administered to diabetic mice stimulates insulin secretion and effectively lowers their blood sugar levels. GLP-1 also enhances β-cell neogenesis and islet size (Stoffers et al., 2000, Diabetes, 49:741–748).

Ferber et al. have demonstrated that adenovirus-mediated in vivo transfer of the PDX-1 (also known as IDX-1) transgene to mouse liver results in the transconversion of a hepatocyte subpopulation towards a β-cell phenotype. It has been demonstrated that after intravenous infusion of mice with the PDX-1 adenoviral vector, up to 60% of hepatocytes synthesized PDX-1. The concentration of immunoreactive insulin was increased in the liver and serum of treated mice. Mice treated with PDX-1 survive streptozotocin-induced diabetes, and can even normalize glycemia (Ferber et al., 2000, Nature Med., 6:568–572).

While ductal cell cultures obtained from isolated islets apparently contain cells that can give rise to insulin-secreting cells, it has remained unclear whether those cells represent true stem cells or merely ductal epithelial cells undergoing transdifferentiation. Even if such preparations contain genuine stem cells, it is unknown what fraction represent stem cells and what contaminating cell types may be present. There is a need in the art for the isolation of specific cell types from pancreatic tissue, the cell types being characterized as stem cells using molecular markers and demonstrated to be pluripotent and to proliferate long-term.

Pluripotent stem cells that are capable of differentiating into neuronal and glial tissues have been identified in brain. Neural stem cells specifically express nestin, an intermediate filament protein (Lendahl et al., 1990; Dahlstrand et al., 1992). Nestin is expressed in the neural tube of the developing rat embryo at day E11, reaches maximum levels of expression in the cerebral cortex at day E16, and decreases in the adult cortex, becoming restricted to a population of ependymal cells (Lendahl et al., 1990). Developing neural and pancreatic islet cells exhibit phenotypic similarities characterized by common cellular markers.

The invention relates to a population of pancreatic islet stem/progenitor cells (IPCs) that are similar to neural and hepatic stem cells and differentiate into islet α-cells (glucagon) and β-cells (insulin). The invention also relates to nestin-positive liver cells. IPCs according to the invention are immunologically silent/immunoprivileged and are recognized by a transplant recipient as self. The IPCs according to the invention can be used for engraftment across allogeneic and xenogeneic barriers.

There is a need in the art for a method of engrafting stem cells across allogeneic and xenogeneic barriers.

There is also a need in the art for a method of treating type I diabetes mellitus wherein islets, nestin-positive pancreatic stem cells or nestin-positive liver stem cells are transferred into a recipient across allogeneic or xenogeneic barriers and graft rejection does not occur.

There is also a need in the art for a method of transplantation into a mammal wherein islets, nestin-positive pancreatic stem cells or nestin-positive liver stem cells are transferred into a recipient across allogeneic or xenogeneic barriers and graft rejection does not occur.

SUMMARY OF THE INVENTION

It is an object of the invention to provide mammalian pancreatic or liver stem cells for use in treating diabetes mellitus and other disorders. It is also an object of the invention to provide methods for identifying, localizing, and isolating pancreatic stem cells. It is a further object of the invention to provide methods for differentiating pancreatic stem cells to obtain cells that produce insulin and other hormones. It is also an object of the invention to provide methods for transplantation into a mammal that utilize mammalian pancreatic or liver stem cells. These and other objects of the invention are provided by one or more of the embodiments described below.

One embodiment of the invention provides a method of treating a patient with diabetes mellitus wherein the patient does not serve as the donor. A nestin-positive pancreatic stem cell is isolated from a pancreatic islet of a donor. The stem cell is transferred into the patient, where it differentiates into an insulin-producing cell.

Another embodiment provides another method of treating a patient with diabetes wherein the patient does not serve as the donor. A nestin-positive pancreatic stem cell is isolated from a pancreatic islet of a donor and expanded ex vivo to produce a progenitor cell. The progenitor cell is transferred into the patient, where it differentiates into an insulin-producing beta cell. Another embodiment provides still another method of treating a diabetes patient wherein the patient does not serve as the donor. A nestin-positive pancreatic stem cell is isolated from a pancreatic islet of a donor and expanded to produce a progenitor cell. The progenitor cell is differentiated in culture to form pseudo-islet like aggregates that are transferred into the patient.

Another embodiment provides another method of treating a patient with diabetes mellitus wherein the patient does not serve as the donor. A nestin-positive pancreatic stem cell is isolated from a pancreatic islet of a donor and cultured ex vivo to produce a progenitor cells. The progenitor cell is transferred into the patient, where it differentiates into an insulin-producing beta cell.

In another preferred embodiment, the patient is a human and the donor is a non-human mammal.

In another preferred embodiment, the patient is not treated with an immunosuppressive agent prior to the transferring step.

In another preferred embodiment, prior to the step of transferring, the stem cell is treated ex vivo with an agent selected from the group consisting of EGF, bFGF-2, high glucose, KGF, HGF/SF, GLP-1, exendin-4, IDX-1, a nucleic acid molecule encoding IDX-1, betacellulin, activin A, TGF-β, and combinations thereof.

In another preferred embodiment, the step of transferring is performed via endoscopic retrograde injection.

In another preferred embodiment, the method of treating a patient with diabetes mellitus additionally comprises the step of treating the patient with an immunosuppressive agent.

In another preferred embodiment, the immunosuppressive agent prevents an immune response.

In another preferred embodiment, the immunosuppressive agent delays the occurrence of an immune response.

In another preferred embodiment, the immunosuppressive agent decreases the intensity of an immune response.

In another preferred embodiment, the immune response is transplant rejection.

In another preferred embodiment, the immunosuppressive agent is selected from the group consisting of FK-506, cyclosporin, and GAD65 antibodies.

As used herein, "differentiation" refers to the process by which a cell undergoes a change to a particular cell type, e.g. to a specialized cell type. The stem cell is treated with an agent selected from the group consisting of EGF, bFGF-2, high glucose, KGF, HGF/SF, IDX-1, a nucleic acid molecule encoding IDX-1, GLP-1, exendin-4, betacellulin, activin A, TGF-β, and combinations thereof. In one embodiment of the invention, the stem cell subsequently differentiates into a pancreatic progenitor cell.

In another preferred embodiment, a pancreatic progenitor subsequently forms pseudo-islet like aggregates.

One embodiment of the invention provides a method of transplanting into a mammal. A nestin-positive pancreatic stem cell is isolated from a pancreatic islet of a donor. The stem cell is transferred into the mammal, where it differentiates into an insulin-producing cell.

Another embodiment provides another method of transplanting into a mammal. A nestin-positive pancreatic stem cell is isolated from a pancreatic islet of a donor and expanded ex vivo to produce a progenitor cell. The progenitor cell is transferred into the mammal, where it differentiates into an insulin-producing beta cell. Another embodiment provides still another method of transplanting into a mammal. A nestin-positive pancreatic stem cell is isolated from a pancreatic islet of a donor and expanded to produce a progenitor cell. The progenitor cell is differentiated in culture to form pseudo-islet like aggregates that are transferred into the mammal.

Another embodiment provides another method of transplanting into a mammal. A nestin-positive pancreatic stem cell is isolated from a pancreatic islet of a donor and cultured ex vivo to produce a progenitor cells. The progenitor cell is transferred into the mammal, where it differentiates into an insulin-producing beta cell.

In these embodiments, the mammal can also serve as the donor of the pancreatic islet tissue, providing an isograft of cells or differentiated tissue.

In a preferred embodiment, the mammal does not serve as the donor of the pancreatic islet tissue.

In another preferred embodiment, the mammal is a human and the donor is a non-human mammal.

In another preferred embodiment, the mammal is not treated with an immunosuppressive agent prior to the transferring step.

In another preferred embodiment, prior to the step of transferring, the stem cell is treated ex vivo with an agent selected from the group consisting of EGF, bFGF-2, high glucose, KGF, HGF/SF, GLP-1, exendin-4, IDX-1, a nucleic acid molecule encoding IDX-1, betacellulin, activin A, TGF-β, and combinations thereof.

In another preferred embodiment, the step of transferring is performed via endoscopic retrograde injection.

In another preferred embodiment, the method of transplanting into a mammal additionally comprises the step of treating the mammal with an immunosuppressive agent.

In another preferred embodiment, the immunosuppressive agent prevents an immune response.

In another preferred embodiment, the immunosuppressive agent delays the occurrence of an immune response.

In another preferred embodiment, the immunosuppressive agent decreases the intensity of an immune response.

In another preferred embodiment, the immune response is transplant rejection.

In another preferred embodiment, the immunosuppressive agent is selected from the group consisting of FK-506, cyclosporin, and GAD65 antibodies.

Yet another embodiment provides an isolated, nestin-positive human pancreatic stem cell that is immunoprivileged. Yet another embodiment provides an isolated, nestin-positive human pancreatic stem cell that does not express class I MHC antigens. Yet another embodiment provides an isolated, nestin-positive human pancreatic stem cell that does not express class II MHC antigens. I Yet another embodiment provides an isolated, nestin-positive human pancreatic stem cell that does not express class I or class I antigens.

Yet another embodiment provides a method of treating a patient with liver disease wherein the patient does not serve as the donor. A nestin-positive pancreatic stem cell is isolated from a pancreatic islet of a donor and transferred into the patient, where the stem cell differentiates into a hepatocyte.

In a related embodiment, the stem cell is expanded ex vivo to a progenitor cell, which is transferred into the patient and further differentiates into a hepatocyte.

In another related embodiment, the stem cell is differentiated ex vivo to a progenitor cell, which is transferred into the patient and further differentiates into a hepatocyte. In another related embodiment, the stem cell is differentiated ex vivo into hepatocytes, which are transplanted into the patient.

In a preferred embodiment, the patient does not serve as the donor of the pancreatic islet tissue.

In another preferred embodiment, the patient is a human and the donor is a non-human mammal.

In another preferred embodiment, the patient is not treated with an immunosuppressive agent prior to the transferring step.

In another preferred embodiment, the method of treating a patient with liver disease additionally comprises the step of treating the patient with an immunosuppressive agent.

In another preferred embodiment, the immunosuppressive agent prevents an immune response.

In another preferred embodiment, the immunosuppressive agent delays the occurrence of an immune response.

In another preferred embodiment, the immunosuppressive agent decreases the intensity of an immune response.

In another preferred embodiment, the immune response is transplant rejection.

Yet another embodiment provides a method of transplanting into a mammal. A nestin-positive pancreatic stem cell is isolated from a pancreatic islet of a donor and transferred into the mammal, where the stem cell differentiates into a hepatocyte.

In a related embodiment, the stem cell is expanded ex vivo to a progenitor cell, which is transferred into the mammal and further differentiates into a hepatocyte.

In another related embodiment, the stem cell is differentiated ex vivo to a progenitor cell, which is transferred into the mammal and further differentiates into a hepatocyte. In another related embodiment, the stem cell is differentiated ex vivo into hepatocytes, which are transplanted into the mammal.

In these embodiments, the mammal can also serve as the donor of the pancreatic islet tissue, providing an isograft of cells or differentiated tissue.

In a preferred embodiment, the mammal does not serve as the donor of the pancreatic islet tissue.

In another preferred embodiment, the mammal is a human and the donor is a non-human mammal.

In another preferred embodiment, the mammal is not treated with an immunosuppressive agent prior to the transferring step.

In another preferred embodiment, the method of transplanting into a mammal additionally comprises the step of treating the mammal with an immunosuppressive agent.

In another preferred embodiment, the immunosuppressive agent prevents an immune response.

In another preferred embodiment, the immunosuppressive agent delays the occurrence of an immune response.

In another preferred embodiment, the immunosuppressive agent decreases the intensity of an immune response.

In another preferred embodiment, the immune response is transplant rejection.

Yet another embodiment provides an isolated, nestin-positive human liver stem cell. In versions of this embodiment, the stem cell is immunoprivileged. In versions of this embodiment, the stem cell does not express class I MHC antigens. In versions of this embodiment, the stem cell does not express class II MHC antigens. In versions of this embodiment, the stem cell does not express class I or class II antigens.

Yet another embodiment provides an isolated, nestin-positive human stem cell that is not a neural stem cell, that is capable of transplant into an animal without causing graft versus host rejection. In versions of this embodiment, the stem cell is not major histocompatibility complex class I or class II restricted.

A "stem cell" as used herein is a undifferentiated cell which is capable of essentially unlimited propagation either in vivo or ex vivo and capable of differentiation to other cell types. This can be to certain differentiated, committed, immature, progenitor, or mature cell types present in the tissue from which it was isolated, or dramatically differentiated cell types, such as for example the erythrocytes and lymphocytes that derive from a common precursor cell, or even to cell types at any stage in a tissue completely different from the tissue from which the stem cell is obtained. For example, blood stem cells may become brain cells or liver cells, neural stem cells can become blood cells, such that stem cells are pluripotential, and given the appropriate signals from their environment, they can differentiate into any tissue in the body.

In one embodiment, a "stem cell" according to the invention is immunologically blinded or immunoprivileged. As used herein, "immunologically blinded" or "immunoprivileged" refers to a cell that does not elicit an immune response. As used herein, an "immune response" refers to a response made by the immune system to a foreign substance. An immune response, as used herein, includes but is not limited to transplant or graft rejection, antibody production, inflammation, and the response of antigen specific lymphocytes to antigen. An immune response is detected, for example, by determining if transplanted material has been successfully engrafted or rejected, according to methods well-known in the art, and as defined herein in the section entitled, "Analysis of Graft Rejection". In one embodiment, an "immunogically blinded stem cell" or an "immunoprivileged stem cell" according to the invention can be allografted or xenografted without transplant rejection, and is recognized as self in the transplant recipient or host.

Transplanted or grafted material can be rejected by the immune system of the transplant recipient or host unless the host is immunotolerant to the transplanted material or unless immunosupressive drugs are used to prevent rejection.

As used herein, a host that is "immunotolerant", according to the invention, fails to mount an immune response, as defined herein. In one embodiment, a host that is "immunotolerant" does not reject or destroy transplanted material. In one embodiment, a host that is "immunotolerant" does not respond to an antigen by producing antibodies capable of binding to the antigen.

As used herein, "rejection" refers to rejection of transplanted material by the immune system of the host. In one embodiment, "rejection" means an occurrence of more than 90% cell or tissue necrosis of the transplanted material in response to the immune response of the host. In another embodiment, "rejection" means a decrease in the viability such that the viability of the transplanted material is decreased by 90% or more as compared to the viability of the transplanted material prior to transplantation, in response to the immune response of the host. A decrease in viability can be determined by methods well known in the art, including but not limited to trypan blue exclusion staining. In another embodiment, "rejection" means failure of the transplanted material to proliferate. Proliferation can be measured by methods known in the art including but not limited to hematoxylin/eosin staining. The occurrence of transplant rejection and/or the speed at which rejection occurs following transplantation will vary depending on factors, including but not limited to the transplanted material (i.e., the cell type, or the cell number) or the host (i.e., whether or not the host is immunotolerant and/or has been treated with an immunosuppressive agent. As used herein, "graft versus host rejection" or "graft versus host response" refers to a cell-mediated reaction in which T-cells of the transplanted material react with antigens of the host.

As used herein, "host versus graft rejection" or "host versus graft response" refers to a cell-mediated reaction in which cells of the host's immune system attack the foreign grafted or transplanted material.

In another embodiment of the invention, an immune response has occurred if production of a specific antibody (for example an antibody that binds specifically to an antigen on the transplanted material, or an antibody that binds specifically to the foreign substance or a product of the foreign substance) is detected by immunological methods well-known in the art, including but not limited to ELISA, immunostaining, immunoprecipitation and Western Blot analysis.

Stem cells express morphogenic or growth hormone receptors on the cell surface, and can sense, for example, injury-related factors then localize to and take residence at sites of tissue injury, or sense their local microenvironment and differentiate into the appropriate cell type.

"Essentially unlimited propagation" can be determined, for example, by the ability of an isolated stem cell to be propagated through at least 50, preferably 100, and even up to 200 or more cell divisions in a cell culture system. Stem cells can be "totipotent," meaning that they can give rise to all the cells of an organism as for germ cells. Stem cells can also be "pluripotent," meaning that they can give rise to many different cell types, but not all the cells of an organism. When a stem cell differentiates it generally gives rise to a more adult cell type, which may be a partially differentiated cell such as a progenitor cell, a differentiated cell, or a terminally differentiated cell. Stem cells can be highly motile.

"Nestin" refers to an intermediate filament protein having a sequence disclosed in Genbank Access No. X65964 (FIG. 7).

A "pancreatic" stem cell means a stem cell that has been isolated from pancreatic tissue and/or a cell that has all of the characteristics of: nestin-positive staining, nestin gene expression, cytokeratin-19 negative staining, long-term proliferation in culture, and the ability to differentiate into pseudo-islets in culture.

A "liver" stem cell means a stem cell that has been isolated from liver tissue and/or a cell that has all of the characteristics of: nestin-positive staining, nestin gene expression, and long-term proliferation in culture.

A "progenitor cell" is a cell that is derived from a stem cell by differentiation and is capable of further differentiation to more mature cell types.

As used herein, the term "insulin-producing beta cell" refers to any cell which can produce and secrete insulin in a similar amount to that produced and secreted by a beta cell of the islets of Langerhans in the human pancreas. Preferably, the secretion of insulin by an insulin-producing beta cell is also regulated in a similar fashion to the regulation of insulin secretion by a human beta cell in situ; for example, insulin secretion should be stimulated by an increase in the glucose concentration in the solution surrounding the insulin-producing beta cell.

"Pseudo-islet like" aggregates are artificial aggregates of insulin-secreting cells which resemble in form and function the islets of Langerhans of the pancreas. Pseudo-islet like aggregates are created ex vivo under cell culture conditions. They are approximately 50–150 $\mu$m in diameter (compared to an average diameter of 100 $\mu$m for in situ islets) and spheroid in form.

"Isolating" a stem cell refers to the process of removing a stem cell from a tissue sample and separating away other cells which are not stem cells of the tissue. An isolated stem cell will be generally free from contamination by other cell types and will generally have the capability of propagation and differentiation to produce mature cells of the tissue from which it was isolated. However, when dealing with a collection of stem cells, e.g., a culture of stem cells, it is understood that it is practically impossible to obtain a collection of stem cells which is 100% pure. Therefore, an isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, or 99% pure. Preferably, isolated stem cells according to the invention will be at least 98% or at least 99% pure.

A stem cell is "expanded" when it is propagated in culture and gives rise by cell division to other stem cells and/or progenitor cells. Expansion of stem cells may occur spontaneously as stem cells proliferate in a culture or it may require certain growth conditions, such as a minimum cell density, cell confluence on the culture vessel surface, or the addition of chemical factors such as growth factors, differentiation factors, or signaling factors.

A stem cell, progenitor cell, or differentiated cell is "transplanted" or "introduced" into a mammal when it is transferred from a culture vessel into a patient. Transplantation, as used herein, can include the steps of isolating a stem cell according to the invention and transferring the stem cell into a mammal or a patient. Transplantation can involve transferring a stem cell into a mammal or a patient by injection of a cell suspension into the mammal or patient, surgical implantation of a cell mass into a tissue or organ of the mammal or patient, or perfusion of a tissue or organ with a cell suspension. The route of transferring the stem cell or transplantation, will be determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

Transplantation, as used herein, can include the steps of isolating a stem cell according to the invention, and culturing and transferring the stem cell into a mammal or a patient. Transplantation, as used herein, can include the steps of isolating a stem cell according to the invention, differentiating the stem cell, and transferring the stem cell into a mammal or a patient. Transplantation, as used herein, can include the steps of isolating a stem cell according to the invention, differentiating and expanding the stem cell and transferring the stem cell into a mammal or a patient.

A "transplant graft" as used herein refers to at least $10^5$ stem cells according to the invention and up to $10^8$ or $10^9$ stem cells.

Treatment with an immunosuppressive agent can be accomplished by administering to a patient in need thereof any agent which prevents, delays the occurrence of or decreases the intensity of the desired immune response, e.g., rejection of a transplanted cell, tissue, or organ.

As used herein, "immunosuppression" refers to prevention of the immune response (for example by the administration of an "immunosuppresive agent", as defined herein) such that an "immune response", as defined herein, is not detectable. As used herein, "prevention" of an immune response means an immune response is not detectable. An immune response (for example, transplant rejection or antibody production) is detected according to methods well-known in the art and defined herein.

"Immunosuppression" according to the invention also means a delay in the occurrence of the immune response as compared to any one of a transplant recipient that has not received an immunosuppresive agent, or a transplant recipient that has been transplanted with material that is not "immunologically blinded" or "immunoprivileged", as defined herein. A delay in the occurrence of an immune response can be a short delay, for example 1 hr–10 days, i.e., 1 hr, 2, 5 or 10 days. A delay in the occurrence of an immune response can also be a long delay, for example, 10 days–10 years (i.e., 30 days, 60 days, 90 days, 180 days, 1, 2, 5 or 10 years).

"Immunosuppression" according to the invention also means a decrease in the intensity of an immune response. According to the invention, the intensity of an immune response can be decreased such that it is 5–100%, preferably, 25–100% and most preferably 75–100% less than the intensity of the immune response of any one of a transplant recipient that has not received an immunosuppresive agent, or a transplant recipient that has been transplanted with material that is not "immunologically blinded" or "immunoprivileged", as defined herein. The intensity of an immune response can be measured by determining the time point at which transplanted material is rejected. For example, an immune response comprising rejection of transplanted material at day 1, post-transplantation, is of a greater intensity than an immune response comprising the rejection of transplanted material at day 30, post-transplantation. The intensity of an immune response can also be measured by quantitating the amount of a particular antibody capable of binding to the transplanted material, wherein the level of antibody production correlates directly with the intensity of the immune response. Alternatively, the intensity of an immune response can be measured by determining the time point at which a particular antibody capable of binding to the transplanted material is detected.

Various strategies and agents can be utilized for immunosuppression. For example, the proliferation and activity of lymphocytes can be inhibited generally with agents such as, for example, FK-506, or cyclosporin or other immunosuppressive agents. Another possible strategy is to administer an antibody, such as an anti-GAD65 monoclonal antibody, or another compound which masks a surface antigen on a transplanted cell and therefore renders the cell practically invisible to the immune system of the host.

An "immunosuppressive agent" is any agent that prevents, delays the occurrence of or reduces the intensity of an immune reaction against a foreign cell in a host, particularly a transplanted cell. Preferred are immunosuppressive agents which suppress cell-mediated immune responses against cells identified by the immune system as non-self. Examples of immunosuppressive agents include but are not limited to cyclosporin, cyclophosphamide, prednisone, dexamethasone, methotrexate, azathioprine, mycophenolate, thalidomide, FK-506, systemic steroids, as well as a broad range of antibodies, receptor agonists, receptor antagonists, and other such agents as known to one skilled in the art.

A "mitogen" is any agent that stimulates mitosis and cell proliferation of a cell to which the agent is applied.

A "differentiation factor" is any agent that causes a stem cell or progenitor cell to differentiate into another cell type. Differentiation is usually accomplished by altering the expression of one or more genes of the stem cell or progenitor cell and results in the cell altering its structure and function.

A "signaling factor" as used herein is an agent secreted by a cell which has an effect on the same or a different cells. For example, a signaling factor can inhibit or induce the growth, proliferation, or differentiation of itself, neighboring cells, or cells at distant locations in the organism. Signaling factors can, for example, transmit positional information in a tissue, mediate pattern formation, or affect the size, shape and function of various anatomical structures.

As used herein, a mammal refers to any mammal including but not limited to human, mouse, rat, sheep, monkey, goat, rabbit, hamster, horse, cow or pig.

A "non-human mammal", as used herein, refers to any mammal that is not a human.

As used herein, "allogeneic" refers to genetically different members of the same species.

As used herein, "isogeneic" refers to of an identical genetic constitution.

As used herein, "xenogeneic" refers to members of a different species.

As used herein, "culturing" refers to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

As used herein, "pre-inducing or inducing a state of immune tolerance" refers to the treatment of a potential transplant recipient with stem cells derived from a transplant donor such that, upon transplantation of an organ, tissue or cells from the donor, the immune system of the recipient recognizes the donor tissue as self and consequently does not initiate a "graft versus host" response. In a preferred embodiment, the stem cells are nestin positive stem cells.

As used herein, "tolerance" refers to a state of the immune system in which certain foreign antigens are recognized by the cells of the immune system as self.

As used herein, a "recipient" refers to a mammal that receives an organ, tissue or cells taken from a donor.

As used herein, a "donor" is a mammal from which organs, tissues or cells are taken for transplant into a recipient.

The invention also provides for a pharmaceutical composition comprising the isolated stem cells of the invention admixed with a physiologically compatible carrier.

BRIEF DESCRIPTION OF THE DRAWINGS

FIG. 7A–7C is the amino acid (SEQ ID NO: 2) and nucleotide (SEQ ID NO: 1) sequences of nestin.

FIG. 8A–8E depict expression of the neural stem cell-specific marker nestin in a distinct cell population within pancreatic islets as determined by immunocytochemistry or RT-PCR.

FIG. 10A–10D depict expression of homeodomain protein IDX-1 and proglucagon in human islet-like clusters derived from nestin-positive islet progenitor cells (NIPs).

FIG. 12 depicts alternative models for the origin of pancreatic duct cells that are progenitors of islet endocrine cells.

DETAILED DESCRIPTION OF THE INVENTION

Figure 1A:
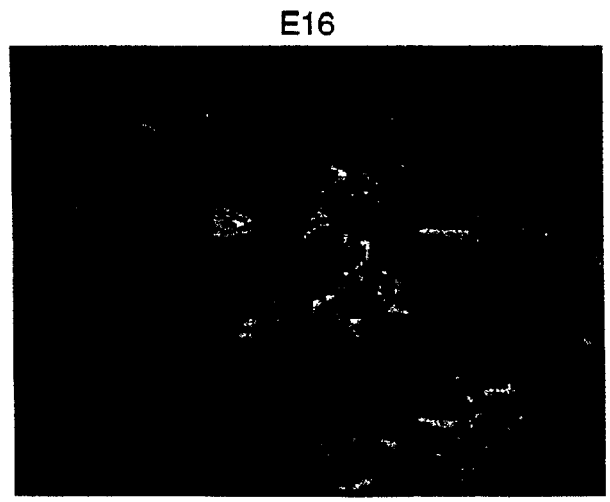
FIGS. 1A and 1B show dual fluorescence immunocytochemical staining of rat pancreatic islets at embryonic day 16 (FIG. 1A) and at day 60 after birth (FIG. 1B). Immunostaining with an antibody for nestin is shown in white (red in the original, with Cy3 as fluorophore) and with an antibody for insulin is shown in grey (green in the original, with Cy2 as fluorophore).

The present inventors have identified and isolated a special subclass of ductal cells from the islets of Langerhans of mammalian pancreas that have the functional and molecular characteristics of stem cells. In particular, these newly discovered pancreatic stem cells are characterized inter alia by one or more (and preferably all of): nestin-positive staining, nestin gene expression, cytokeratin-19 negative staining, long-term proliferation in culture, and the ability to differentiate into pseudo-islets in culture. The present inventors have also identified liver cells that exhibit nestin-positive staining.

In one embodiment, the invention provides stem cells for a variety of applications, including but not limited to cellular replacement therapy for type I insulin-dependent diabetes and other forms of diabetes as well as the development of research tools to study the onset and progression of various diabetic conditions, hormonal abnormalities, and genetic diseases or conditions, such as the association of polymorphisms with particular physiologic or pathologic states. The stem cells of the invention can also be used to carry out gene therapy of endocrine pancreatic or other tissues in isograft, allograft or xenograft transplantations. Further, the stem cells described herein can be used to produce recombinant cells, artificial tissues, and replacement organs in culture. They can also be used for the ex vivo production of insulin and other hormones. Molecular characteristics of pancreatic stem cells discovered by the inventors, such as nestin-positive and cytokeratin-19 negative staining, or liver stem cells, such as nestin-positive staining, can be used in various diagnostic, pathological, or investigative procedures to identify, localize, and quantitate stem cells in tissues from a patient or experimental animal.

Identification of Stem Cells in Pancreatic Islets

Previous investigators have focused on ductal epithelial cells of pancreatic islets or exocrine tissue as a possible source of stem cells for the neogenesis of islet endocrine cells. Nestin is an intermediate filament protein that was cloned by screening a cDNA library from E15 rat embryos with a monoclonal antibody named R.401 (Hockfield & McKay, 1985; Lendahl et al., 1990). Nestin was primarily found in neuroepithelial stem cells and is expressed in the developing central nervous system. After maximum levels are reached in the rat embryo at E16, nestin expression declines to almost undetectable levels in adult cerebral cortex, coinciding with terminal differentiation of early nestin-expressing progenitor cells (Lendahl et al., 1990). Nestin was initially found exclusively in stem cells of the embryonic developing brain and skeletal muscle (Lendahl et al., 1990). Later studies identified nestin-positive neural stem cells in the subependymal layer of the adult mammalian forebrain (Morshead et al., 1994). Nestin-positive stem cells have been shown to be pluripotential even when isolated from adult mice or rat brain. For example, nestin-positive stem cells can generate all three major classes of neural cells in culture: neurons, astrocytes, and oligodendrocytes (Reynolds & Weiss, 1996). Nestin-positive neural stem cells respond to spinal cord injury by proliferation and degeneration of migratory cells that differentiate into astrocytes, participate in scar formation (Johansson et al., 1999) and restore hematopoietic cells of the bone marrow after infusion into irradiated mice (Bjornson et al., 1999).

Characterization of Stem Cells

Stem cells according to the invention can be identified by their expression of nestin by, for example, FACS, immunocytochemical staining, RT-PCR, Southern Northern and Western blot analysis, and other such techniques of cellular identification as known to one skilled in the art.

Immunocytochemical staining, for example, is carried out according to the following method. Cryosections (6 μM) prepared from pancreata or liver, as well as cells, are fixed with 4% paraformaldehyde in phosphate. Cells are first blocked with 3% normal donkey serum for 30 min at room temperature and incubated with a primary antisera to the protein of interest overnight at 4° C. The antisera is rinsed off with PBS and incubated with the appropriate fluorescently labeled secondary antisera for 1 hour at room temperature. Slides are then washed with PBS and coverslipped with fluorescent mounting medium (Kirkegaard and Perry Labs, Gaithersburg, Md.). Fluorescence images are obtained using a Zeiss Epifluorescence microscope equipped with an Optronics TEC-470 CCD camera (Optronics Engineering, Goleta, Calif.) interfaced with a PowerMac 7100 installed with IP Lab Spectrum analysis software (Signal Analytics Corp, Vienna, Va.).

Antisera useful according to the invention include the following: mouse monoclonal antibodies to human cytokeratin 19 (clone K4.62, Sigma, St. Louis, Mo.), rabbit polyclonal antisera to rat nestin and to IDX-1 (prepared by immunizations of rabbits with a purified GST-nestin fusion protein or the last twelve amino acids of rat IDX-1, respectively) (McManus et al., 1999, J. Neurosci., 19:9004–9015), guinea pig anti-insulin and anti-pancreatic polypeptide antisera, obtained from Linco, St. Charles, Mo., and mouse antiglucagon and rabbit antisomatostatin antisera, purchased from Sigma (St. Louis, Mo.) and DAKO (Carpinteria, Calif.), respectively, mouse anti-human galanin (Peninsula Laboratories, Belmont, Calif.), collagen IV antisera (Caltag Laboratories, San Francisco, Calif.), mouse anti-rat MHC class I serum (Seroteck), and antirat MHC class II serum. The invention contemplates that other antisera directed to such markers is available, or will be developed. Such other antisera is considered to be within the scope of the invention.

RT-PCR and Southern blot analysis are performed according to the following methods. Total cellular RNA prepared from rat or human islets is reverse transcribed and amplified by PCR for about 35 cycles depending on the desired degree of amplification, as described previously (Daniel, et al., 1998, Endocrinology, 139:3721–3729). Oligonucleotides used as primers or amplimers for the PCR and as probes for subsequent Southern blot hybridization are:

| | |
|---|---|
| Rat nestin: | Forward, 5'gcggggcggtgcgtgactac3';<br>(SEQ ID NO: 3);<br>Reverse, 5'aggcaagggggaagagaaggatgt3';<br>(SEQ ID NO: 4);<br>Hybridization, 5'aagctgaagccgaatttccttgggatacca-gagga3'.<br>(SEQ ID NO: 5). |
| Rat keratin 19: | Forward, 5'acagccagtacttcaagacc3';<br>(SEQ ID NO: 6);<br>Reverse, 5'ctgtgtcagcacgcacgtta3';<br>(SEQ ID NO: 7);<br>Hybridization, 5'tggattccacaccaggcattgaccatgcca3'.<br>(SEQ ID NO: 8). |
| Rat NCAM: | Forward, 5'cagcgttggagagtccaaat3';<br>(SEQ ID NO: 9);<br>Reverse, 5'ttaaactcctgtggggttgg3';<br>(SEQ ID NO: 10);<br>Hybridization, 5'aaaccagcagcggatctcagtggtgtgg-accgatgat3'.<br>(SEQ ID NO: 11). |
| Rat IDX-1 | Forward, 5'atcactggagcagggaagt3'<br>(SEQ ID NO: 12)<br>Reverse, 5'gctactacgtttcttatct3'<br>(SEQ ID NO: 13)<br>Hybridization, 5'gcgtggaaaagccagtggg3'<br>(SEQ ID NO: 14) |
| Human nestin: | Forward, 5'agagggggaattcctggag3';<br>(SEQ ID NO: 15)<br>Reverse, 5'ctgaggaccaggactctcta3';<br>(SEQ ID NO: 16)<br>Hybridization, 5'tatgaacgggctggagcagtctgaggaaa-gt3'.<br>(SEQ ID NO: 17) |

-continued

| | |
|---|---|
| Human keratin: | Forward, 5'cttttcgcgcgcccagcatt3';<br>(SEQ ID NO: 18)<br>Reverse, 5'gatcttcctgtccctcgagc3';<br>(SEQ ID NO: 19)<br>Hybridization, 5'aaccatgaggaggaaatcagtacgctga-gg3'.<br>(SEQ ID NO: 20) |
| Human glucagon: | Forward, 5'atctggactccaggcgtgcc3';<br>(SEQ ID NO: 21)<br>Reverse, 5'agcaatgaattccttggcag3';<br>(SEQ ID NO: 22)<br>Hybridization, 5'cacgatgaatttgagagacatgctgaa-ggg3';<br>(SEQ ID NO: 23) |
| Human E-Cadherin | Forward, 5'agaacagcacgtacacagcc3'<br>(SEQ ID NO: 24)<br>Reverse, 5'cctccgaagaaacagcaaga3'<br>(SEQ ID NO: 25)<br>Hybridization, 5'tctcccttcacagcagaactaacacacggg3'<br>(SEQ ID NO: 26) |
| Human transthyretin | Forward, 5'gcagtcctgccatcaatgtg3'<br>(SEQ ID NO: 27)<br>Reverse, 5'gttggctgtgaataccacct3'<br>(SEQ ID NO: 28)<br>Hybridization, 5'ctggagagctgcatgggctcacaactga-gg3'<br>(SEQ ID NO: 29) |
| Human Pancreatic Amylase | Forward, 5'gactttccagcagtcccata3'<br>(SEQ ID NO: 30)<br>Reverse, 5'gtttacttcctgcagggaac3'<br>(SEQ ID NO: 31)<br>Hybridization, 5'ttgcactggagaaggattacgtggcgtt-cta3'<br>(SEQ ID NO: 32) |
| Human procarboxy-peptidase | Forward, 5'tgaaggcgagaaggtgttcc3'<br>(SEQ ID NO: 33)<br>Reverse, 5'ttcgagatacaggcagatat3'<br>(SEQ ID NO: 34)<br>Hybridization, 5'agttagacttttatgtcctgcctgtgctca 3'<br>(SEQ ID NO: 35) |
| Human Synaptophysin | Forward, 5'cttcaggctgcaccaagtgt3'<br>(SEQ ID NO: 36)<br>Reverse, 5'gttgaccatagtcaggctgg3'<br>(SEQ ID NO: 37)<br>Hybridization, 5'gtcagatgtgaagatggccacagaccc-aga 3'<br>(SEQ ID NO: 38) |
| Human Hepatocyte Growth Factor (HGF) | Forward, 5'gcatcaaatgtcagccctgg3'<br>(SEQ ID NO: 39)<br>Reverse, 5'caacgctgacatggaattcc3'<br>(SEQ ID NO: 40)<br>Hybridization, 5'tcgaggtctcatggatcatacagaatcagg 3'<br>(SEQ ID NO: 41) |
| Human cMET (HGF-receptor) | Forward, 5'caatgtgagatgtctccagc3'<br>(SEQ ID NO: 42)<br>Reverse, 5'ccttgtagattgcaggcaga3'<br>(SEQ ID NO: 43)<br>Hybridization, 5'ggactcccatccagtgtctccagaagtgat 3'<br>(SEQ ID NO: 44) |
| Human XBP-1 | Forward, 5'gagtagcagctcagactgcc3'<br>(SEQ ID NO: 45)<br>Reverse, 5'gtagacctctgggagctcct3'<br>(SEQ ID NO: 46)<br>Hybridization, 5'cgcagcactcagactacgtgcacctctg-ca 3'<br>(SEQ ID NO: 47) |
| Human Glut-2 | Forward, 5'gcagctgctcaactaatcac3'<br>(SEQ ID NO: 48)<br>Reverse, 5'tcagcagcacaagtcccact3'<br>(SEQ ID NO: 49)<br>Hybridization, 5'acgggcattcttattagtcagattattggt 3'<br>(SEQ ID NO: 50) |
| Human Insulin | Forward, 5'aggcttcttctacaca3'<br>(SEQ ID NO: 51)<br>Reverse, 5'caggctgcctgcacca3'<br>(SEQ ID NO: 52)<br>Hybridization, 5'aggcagaggacctgca 3'<br>(SEQ ID NO: 53) |

Other such sequences are possible and such sequences are considered to be within the scope of the art. As a general guide, primers are selected from two different exons and encompass at least one intronic sequence. In addition, an RT minus control is run for most samples. PCR amplification is effectuated at 94° C. for 1 min followed by 94° C. for 10 secs, 58/56° C. for 10 secs, 72° C. for 1 min, 35 cycles, and 72° C. for 2 min. The annealing temperature is 58° C. for rat nestin and 56° C. for the remaining primer pairs.

For RT-PCR of mRNA isolated from a mammal that is not rat or human, oligonucleotides that are specific for the amplified nucleic acid from the mammalian species being analyzed are prepared. The selection and use of such primers is known to one skilled in the art.

For Southern hybridization oligonucleotide probes are labeled with an appropriate radionuclide, such as $\gamma^{32}P$ ATP, using conventional techniques. Radiolabeled probes are hybridized to PCR products transferred to nylon membranes at 37° C. for one hour, then washed in 1×SSC+0.5% SDS at 55° C. for 10–20 min or 0.5×SCC+0.5% SDS at 42° for the human PCR products.

Nestin as a Marker of Pancreatic Stem Cells

Figure 1B:
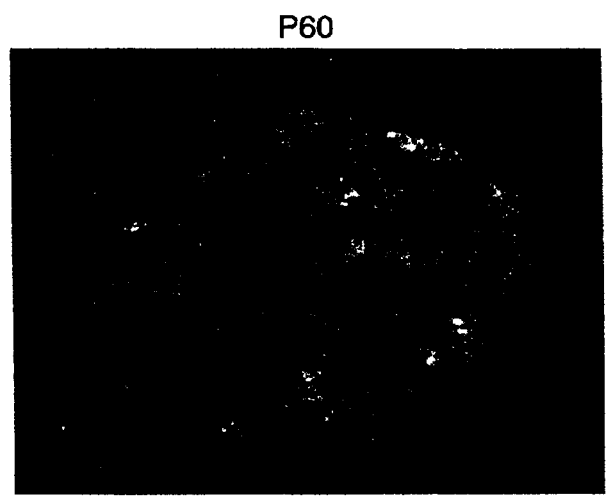

The inventors have now unexpectedly discovered that the pancreas of adult mammals, including humans, contains cells that express nestin. Importantly, the distribution of nestin-positive cells in the pancreas does not correspond to the distribution of hormone-producing cells. For example, fluorescently labeled antibodies specifically reactive to insulin or glucagon label the beta and alpha cells of the islets, respectively, whereas the inventors have observed that in mice, rats, and humans, fluorescently labeled nestin antibodies localize only to certain cells of the ductular epithelium and not to alpha, beta, delta, and pancreatic peptide producing cells in pancreatic islets (FIG. 1). The inventors also observed that antibodies specific for collagen IV, a marker for vascular endothelial cells, galanin, a marker of nerve endings, and cytokeratin 19, a marker for ductal cells, do not colocalize with nestin antibodies. Furthermore, the inventors have found that nestin-positive islet cells do not co-label with antibodies for insulin, glucagon, somatostatin, or pancreatic polypeptide (FIG. 1). This suggests that these nestin-containing cells are not endocrine cells, ductal cells, neural cells, or vascular endothelial cells, but may represent a truly distinct cell type within the islet that has not previously been described. The inventors have found nestin-positive cells in the islets, as well as localized regions of the pancreatic ducts, and within centroacinar regions of the exocrine pancreas.

Figure 2:
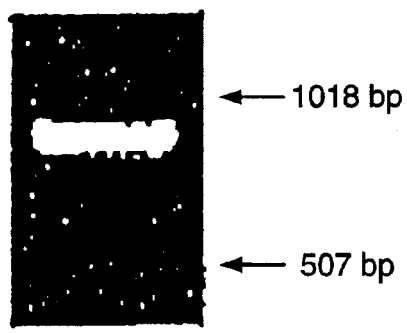
FIG. 2 shows the result of RT-PCR performed using mRNA obtained from 50 rat islets. Forward and reverse primers are indicated. The depicted Primer sequences are: forward primer (SEQ ID NO: 3) and reverse primer (SEQ ID NO: 55). The single band of 834 bp was sequenced and identified substantially as the sequence for nestin.

The expression of nestin mRNA in isolated islets was detected using RT-PCR with RNA from isolated rat islets (FIG. 2). The functional properties of nestin-positive pancreatic cells were investigated using cell culture techniques and by the isolation of nestin-positive cells from islets, both of which are described below.

The inventors have also discovered that the liver of rats contains cells that express nestin (FIG. 13).

Cytokeratin-19 as a Marker for a Distinct Population of Duct Epithelial Cells

Cytokeratin-19 (CK-19) is another intermediate filament protein. CK-19 and related cytokeratins have previously been found to be expressed in pancreatic ductal cells (Bouwens et al., 1994). The inventors have discovered, however, that while CK-19 expression is indeed confined to the ductules, fluorescent antibodies specific for CK-19 label distinct ductal cells from those labeled with nestin-specific antibodies. This suggests that nestin-positive cells in islets may be a distinct cell type of ductal cell from CK-19 positive cells.

Isolated Stem Cells from Pancreatic Islets and Their Use

Stem cells can be isolated from a preparation of pancreatic tissue, for example, islets obtained from a biopsy sample of tissue from a diabetic patient. The stem cells can then be expanded ex vivo and the resulting cells transplanted back into the donor as an isograft. Inside the donor, they may differentiate to provide insulin-secreting cells such as beta cells to replace beta cells lost to the autoimmune attack which caused the diabetes. This approach can overcome the problems of immune rejection resulting from transplantation of tissue, for example, islets from another individual who might serve as the donor. In one embodiment of the invention, the use of isografted stem cells allows another technique to be performed in an effort to avoid the immune rejection, namely genetic therapy of the transplanted cells to render them resistant to immune attack, such as the autoimmunity present in individuals with type 1 diabetes. A further advantage of using stem cells over whole islets is that transplanted stem cells can differentiate in situ and better adapt to the host environment, for example, providing appropriate microcirculation and a complement of different islet cell types which responds to the physiological needs of the host. Another embodiment of the invention contemplates the use of partially differentiated stem cells ex vivo, for example, to form progenitor cells, which are subsequently transplanted into the host, with further differentiation optionally taking place within the host. Although the use of an isograft of stem cells, progenitor cells, or pseudo-islets is preferred, another embodiment contemplates the use of an allograft of stem cells, progenitor cells, or pseudo-islets obtained from another individual or from a mammal of another species.

In yet another embodiment of the invention, the stem cells are immunologically blind or immunoprivileged. In one embodiment of this aspect of the invention, immunoprivileged stem cells do not express sufficient amounts of class I and/or class II major histocompatibility antigens (a.k.a. HLA or human leukocyte antigen) to elicit an immune response from the host. For example, these stem cells, obtained from allogeneic or xenogeneic sources do not initiate a host versus graft response in immunocompetent transplant recipients.

In another embodiment of this aspect of the invention, immunoprivileged stem cells do not express class I MHC antigens and/or class II MHC antigens. These stem cells, obtained from allogeneic or xenogeneic sources do not initiate a host versus graft response in immunocompetent transplant recipients.

In another embodiment of the invention, human tissue grafts comprising stem cells express both human specific class I and class II MHC antigens, but are recognized by immunocompetent mice as self, and do not undergo host versus graft rejection. These stem cells, obtained from allogeneic or xenogeneic sources do not initiate a host versus graft response in immunocompetent transplant recipients.

The invention also provides for methods of isolating stem cells from a xenogenic donor, and transplanting the resulting cells into a mammal of another species (e.g. murine stem cells are transplanted into a human, for example, a diabetic human patient) as a xenograft.

The invention provides for methods of performing isogeneic, allogeneic or xenogeneic transplants of nestin-positive stem cells wherein the stem cells are cultured for a period of time, for example, 2–4 hours, 4–5 hours, 5–10 hours or 1–3 days prior to transplantation.

The invention also provides for methods of performing isogeneic, allogeneic or xenogeneic transplants of nestin-positive stem cells wherein the stem cell is expanded for a period of time, for example, 2–4 hours, 4–5 hours, 5–10 hours or 1–3 days prior to transplantation to give rise by cell division to other stem cells or progenitor cells.

The invention also provides for methods of performing isogeneic, allogeneic or xenogeneic transplants of stem cells wherein the nestin-positive stem cells are induced to differentiate into a progenitor cell by treatment with an agent selected from the group consisting of EGF, bFGF-2, high glucose, KGF, HGF/SF, IDX-1, a nucleic acid molecule encoding IDX-1, GLP-1, exendin-4, betacellulin, activin A, TGF-β, and combinations thereof for a period of time, for example, 2–4 hours, 4–5 hours, 5–10 hours or 1–3 days prior to transplantation. In the case of a pancreatic stem cell, the stem cell subsequently differentiates into a pancreatic progenitor cell.

The invention provides for methods of performing isogeneic, allogeneic or xenogeneic transplants wherein nestin-positive stem cells are not cultured, expanded or differentiated prior to transplantation or wherein nestin-positive stem cells are cultured and/or expanded and/or differentiated prior to transplantation.

Nestin-positive cells can be proliferated in culture from isolated pancreatic islets and subsequently isolated to form a stem cell line capable of essentially unlimited propagation.

Figure 3:
FIG. 3 shows nestin-positive cells that have proliferated out from a cultured rat islet.

The inventors discovered that nestin expressing cells grow out of cultured islets and can be observed growing around the islets as early as about four days in culture. These cells have a neuron-like morphology (FIG. 3), show nestin-positive staining, and express nestin mRNA. Islets containing nestin-positive cells can be separated from other cells, e.g., fibroblasts, that proliferate from the cultured islets by exposing a suspension of the islets to concanavalin A. The islets containing nestin-positive stem cells will not adhere to a concanavalin A coated culture vessel, for example, allowing the islets to be simply decanted while other cell types remain attached to the vessel. The islets are then plated on wells that do not have a concanavalin A coating, where they adhere. The details of the culture and isolation procedure are described for rat cells in Example 1 below. Similar results have been obtained with human cells.

Formation of Pseudo-Islets and Ductal Structures in Culture

One embodiment of the invention provides an alternative to transplantation of stem cells or progenitor cells by causing them to form pseudo-islet like aggregates that can be transplanted into a patient with insufficient islet cell mass to maintain physiological control without hormone therapy. Islet-derived stem cells can be prepared from cultured islets as indicated above or obtained from a propagating stem cell line. The stem cells can then be induced to differentiate by exposing them to various growth factors. This process is illustrated in Examples 2 and 3.

Differentiation of Stem Cells or Progenitor Cells to Islet Cells

Growth factors that may induce differentiation of pancreatic stem cells include but are not limited to EGF-2, basic FGF, high glucose, KGF, HGF/SF, GLP-1, exendin-4, betacellulin, activin A, TGF-β, and combinations thereof. GLP-1 refers to glucagon-like peptide-1. High glucose refers to a higher glucose concentration than the concentration normally used in culturing the stem cells. For example, the stem cells can be normally cultured and propagated in about 5.6 mM glucose, and the high glucose concentration refers to another concentration above 5.6 mM. In the preferred embodiment, a concentration of 16.7 mM is contemplated. In Example 2, one possible growth factor treatment is described using basic fibroblast growth factor (bFGF) and epidermal growth factor (EGF).

In addition to growth factors added to the medium of cultured cells, further growth factors can contribute to differentiation when stem cells are implanted into an animal or a human. In that situation, many growth factors which are either known or unknown may be secreted by endogenous cells and exposed to the stem cells in situ. Implanted stem cells can be induced to differentiate by any combination of endogenous and exogenously administered growth factors that are compatible with the desired outcome, i.e., the final differentiated cell type or types and the anatomical structures (e.g., tissues or organs) formed.

One embodiment provides an approach to stimulating differentiation, that is to administer downstream effectors of growth factors or to transfect stem cells or progenitor cells with a nucleic acid molecule encoding such effectors. One example is IDX-1, which is a transcription factor induced by GLP-1 or exendin-4. Introducing effectors such as IDX-1 can trigger differentiation to form endocrine islet cells.

Analysis of Graft Rejection

The invention provides for an in vivo procedure for evaluating the survival of transplanted material. Experimental transplant rejection is analyzed by transplanting an immunosuppressed or a non-immunosuppressed mammal, with a stem cell or a pseudo-islet like aggregate according to the invention.

For example, non-immunosuppressed C57BL/6 mice are transplanted (for example, under the renal capsules) with human stem cells according to the invention. Graft rejection is analyzed by sacrificing the transplant recipient and staining for viability, or performing immunocytochemical staining at the site of the grafted material (i.e., an organ or tissue present at the site of the grafted material) at a suitable post-transplantation time point. The time point at which staining (for example hematoxylinleosin or immunostaining) of the site of the grafted material is made can vary, for example, according to the average survival time, or the expected survival time of a transplanted mammal. The site of the graft is analyzed, for example by staining, 1 day to 10 years (i.e., 1, 5, 10, 30, 100 or more days, 1, 2, 5, or 10 years) post-transplantation, preferably 10 days to 1 year post-transplantation and most preferably, 10–100 days post-transplantation. For example, if transplanted material is introduced under the renal capsule of a mouse, the kidney of the transplanted mouse is inspected. Transplanted material is successfully engrafted (i.e., not rejected) if, the transplanted material is still detectable and/or the transplanted material has proliferated into a tissue mass.

Detection of the transplanted material and proliferation of the transplanted material is determined, for example, by hematoxylin/eosin staining of a frozen section prepared from the transplant site (i.e., the kidney) and the detection of new growth that is not derived from the transplant recipient (i.e., not host kidney derived). In the case of xenogeneic transplantation, transplanted material is successfully engrafted if specific immunostaining with antisera specific for an antigen from the species from which the transplanted material is derived, according to methods of immunocytochemical staining known in the art and described herein, identifies positive cells. Alternatively, in embodiments wherein a xenogeneic transplantation is performed, transplanted material is successfully engrafted if molecules (i.e., a protein or an antigen) derived from the transplant species (that is the species from which the transplanted material is derived) are detected in the blood of the transplant recipient. As used herein, "rejection" refers to rejection of transplanted material by the immune system of the host. In one embodiment, "rejection means an occurrence of more than 90% cell or tissue necrosis of the transplanted material in response to the immune response of the host. In another embodiment, "rejection" means a decrease in the viability such that the viability of the transplanted material is decreased by 90% or more as compared to the viability of the transplanted material prior to transplantation, in response to the immune response of the host. A decrease in viability can be determined by methods well known in the art, including but not limited to trypan blue exclusion staining. In another embodiment, "rejection" means failure of the transplanted material to proliferate. Proliferation can be measured by methods known in the art including but not limited to hematoxylin/eosin staining. The occurrence of transplant rejection and/or the speed at which rejection occurs following transplantation will vary depending on factors, including but not limited to the transplanted material (i.e., the cell type, or the cell number) or the host (i.e., whether or not the host is immunotolerant and/or has been treated with an immunosuppressive agent.

Methods of Transplantation

The invention provides for methods of transplantation in to a mammal. A stem cell, progenitor cell, or differentiated cell is "transplanted" or "introduced" into a mammal when it is transferred from a culture vessel into a patient.

Transplantation, according to the invention can include the steps of isolating a stem cell according to the invention and transferring the stem cell into a mammal or a patient. Transplantation according to the invention can involve transferring a stem cell into a mammal or a patient by injection of a cell suspension into the mammal or patient, surgical implantation of a cell mass into a tissue or organ of the mammal or patient, or perfusion of a tissue or organ with a cell suspension. The route of transferring the stem cell or transplantation, will be determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

Transplantation, according to the invention, can include the steps of isolating a stem cell according to the invention, and culturing and transferring the stem cell into a mammal or a patient. In another embodiment, transplantation, as used herein, can include the steps of isolating a stem cell according to the invention, differentiating the stem cell, and transferring the stem cell into a mammal or a patient.

Transplantation, as used herein, can include the steps of isolating a stem cell according to the invention, differentiating and expanding the stem cell and transferring the stem cell into a mammal or a patient.

Methods of Treating Insulin-Dependent Diabetes Using Pancreatic Stem Cells

Stem cells are useful to replace lost beta cells from Type 1 diabetes patients or to increase the overall numbers of beta cells in Type 2 diabetes patients. The diabetes patient will preferably serve as the donor of pancreatic tissue used to produce stem cells, progenitor cells, or pseudo-islet like aggregates. Stem cells exist within the adult pancreatic islets as well as the pancreatic ducts. After a diabetic patient undergoes pancreatic biopsy, islets are isolated from the biopsy tissue and prepared for culture ex vivo preferably within 24 hours. Stem cells can be proliferated and isolated by the methods described above within 2–3 weeks. Stem cells can be transplanted back into the patient directly following isolation or after a period of differentiation which is induced by growth factors. Islets can be produced by subculture as described in Example 2. The whole process of surgical pancreas biopsy and transplantation can be performed within a period of about 30 days.

In one embodiment of the invention, pluripotential stem cells are used. These cells are immunologically blinded or immunoloprivileged, such that in allogeneic or xenogeneic transplants, they are recognized as self by the recipient, and are not MHC restricted by class I or class II antigens. In one aspect of this embodiment of the invention, these cells do not express MHC class I and/or class II antigens.

In another embodiment of the invention, the recipient of the transplant may demonstrate host vs. graft rejection of other transplanted cells, which can be combated by the administration of blocking antibodies to, for example, an autoantigen such as GAD65, by the administration of one or more immunosuppressive drugs described herein, or by any method known in the art to prevent or ameliorate autoimmune rejection.

Alternatively, stem cells isolated from a non-human mammal according to the invention, are transplanted into a human diabetes patient. Prior to the transplantation step the stem cells may be cultured, and/or expanded and/or differentiated.

Methods of Treating Patients Suffering from Liver Disease Using Pancreatic Stem Cells The ability of pancreatic stem or progenitor cells to transdifferentiate to form hepatocytes is well known (Bisgaard & Thorgeirsson, 1991). The pancreatic stem cells of the present invention can be used to provide hepatocytes for a patient suffering from a liver disease such as cirrosis, hepatitis, or hepatic cancer in which the functional mass of hepatic tissue has been reduced. The stem cells of the invention can also be treated by gene therapy to correct a genetic defect and introduced into a patient to restore hepatic function. Nestin-positive stem cells can be differentiated either in culture or in vivo by applying one or more growth factors, or other treatment such as transfection with a nucleic acid molecule, that results in differentiation of the stem cells to hepatocytes. In one embodiment, the invention contemplates the use of cyclopamine to suppress, for example, sonic hedgehog, resulting in hepatocyte formation. In another embodiment of the invention, the stem cells can be transplanted without any ex vivo treatment and the appropriate growth factors can be provided in situ within the patient's body. In yet another embodiment, the stem calls can be treated with growth factors or other agents ex vivo and subsequently transplanted into the patient in a partially differentiated or terminally differentiated state. Other aspects of the invention, including methods of transfecting stem cells or progenitor cells, dosages and routes of administration, pharmaceutical compositions, donor-isograft protocols, and immunosuppression methods, can be practiced with transdifferentiation to hepatocytes just as for the differentiation to pancreatic tissues.

The invention specifically contemplates transplanting into patients isogeneic, allogeneic, or xenogeneic stem cells, or any combination thereof.

Methods of Stem Cell Transfection

A variety of methods are available for gene transfer into pancreatic stem cells. Calcium phosphate precipitated DNA has been used but provides a low efficiency of transformation, especially for nonadherent cells. In addition, calcium phosphate precipitated DNA methods often result in insertion of multiple tandem repeats, increasing the likelihood of disrupting gene function of either endogenous or exogenous DNA (Boggs, 1990). The use of cationic lipids, e.g., in the form of liposomes, is also an effective method of packaging DNA for transfecting eukaryotic cells, and several commercial preparations of cationic lipids are available. Electroporation provides improved transformation efficiency over the calcium phosphate protocol. It has the advantage of providing a single copy insert at a single site in the genome. Direct microinjection of DNA into the nucleus of cells is yet another method of gene transfer. It has been shown to provide efficiencies of nearly 100% for short-term transfection, and 20% for stable DNA integration. Microinjection bypasses the sometimes problematic cellular transport of exogenous DNA through the cytoplasm. The protocol requires small volumes of materials. It allows for the introduction of known amounts of DNA per cell. The ability to obtain a virtually pure population of stem cells would improve the feasibility of the microinjection approach to targeted gene modification of pancreatic stem cells. Microinjection is a tedious, highly specialized protocol, however. The very nature of the protocol limits the number of cells that can be injected at any given time, making its use in large scale production limited. Gene insertion into pancreatic stem cells using retroviral methods is the preferred method. Retroviruses provide a random, single-copy, single-site insert at very high transfection efficiencies. Other such transfection methods are known to one skilled in the art and are considered to be within the scope of this invention.

Retroviral Transformation Of Pancreatic Stem Cells

Gene transfer protocols for pancreatic cells can involve retroviral vectors as the "helper virus" (i.e., encapsidation-defective viral genomes which carry the foreign gene of interest but is unable to form complete viral particles). Other carriers such as DNA-mediated transfer, adenovirus, SV40, adeno-associated virus, and herpes simplex virus vectors can also be employed. Several factors should be considered when selecting the appropriate vector for infection. It is sometimes preferable to use a viral long terminal repeat or a strong internal promoter to express the foreign gene rather than rely on spliced subgenomic RNA.

The two primary methods of stem cell transformation are co-culture and supernatant infection. Supernatant infection involves repeated exposure of stem cells to the viral supernatant. Co-culture involves the commingling of stem cells and an infected "package cell line" (see below) for periods of 24 to 48 hours. Co-culture is typically more efficient than supernatant infection for stem cell transformation. After co-culture, infected stem cells are often further cultured to establish a long term culture (LTC).

The cell line containing the helper virus is referred to as the package cell line. A variety of package cell lines are currently available. An important feature of the package cell line is that it does not produce replication-competent helper virus.

In one embodiment of the invention animals or patients from whom stem cells are harvested may be treated with 5-fluorouracil (5-FU) prior to extraction. 5-FU treated stem cells are more susceptible to retroviral infection than untreated cells. 5-FU stem cells dramatically reduce the number of clonogenic progenitors, however.

In another embodiment, harvested stem cells may be exposed to various growth factors, such as those employed to promote proliferation or differentiation of pancreatic stem cells. Growth factors can be introduced in culture before, during, or after infection to improve cell replication and transduction. Studies report the use of growth factors increase transformation efficiency from 30 to 80%.

Typical Retroviral Transformation Protocol

The ex vivo transduction of mammalian pancreatic stem cells and subsequent transplantation into nonablated recipients sufficient to obtain significant engraftment and gene expression in various tissues containing their progeny cells has been shown in mice. The target cells are cultured for 2–4 days in the presence of a suitable vector containing the gene of interest, before being injected in to the recipient.

Specifically, bone marrow stem cells were harvested from male donor (4–8 weeks old) BALB/c AnNCr mice (National Cancer Institute, Division of Cancer Treatment Animal Program, Frederick, Md.). The cells were plated at a density of $1-2\times10^7$ cells/10 cm dish and cultured for 48 hours in Dulbecco's modified Eagle's medium (DMEM) containing; 10% heat-inactivated fetal bovine serum, glutamine, Pen/Strep, 100 U/ml of interleukin-6 (IL-6) and stem cell factor (SCF; Immunex, Seattle, Wash.) to stimulate cell growth (Schiffmann, et. al., 1995).

Concurrently, a viral package cell line was cultured for 24 hours. The package cell line used by Schiffmann, et al. was GP+E86 and the viral vector was the LG retroviral vector based on the LN series of retroviral vectors.

After the appropriate incubation period, $1-2\times10^7$ stem cells were plated on a 10 cm dish containing the viral package cells and co-cultured for 48 hours in the presence of 8 $\mu$g/ml of polybrene and under the same growth factor stimulation conditions as the donor stem cells. The stem cells were then harvested, washed of growth media and injected into recipient mice at dosages of $2\times10^7$ cells/injection for multiple injections (total of 5 injections either daily or weekly).

Successful stem cell transduction and engraftment of stem cells can be determined through, for example, PCR analysis, immunocytochemical staining, Southern Northern or Western blotting, or by other such techniques known to one skilled in the art.

Mammals

Mammals that are useful according to the invention include any mammal (for example, human, mouse, rat, sheep, rabbit, goat, monkey, horse, hamster, pig or cow). A non-human mammal according to the invention is any mammal that is not a human, including but not limited to a mouse, rat, sheep, rabbit, goat, monkey, horse, hamster, pig or a cow.

Dosage and Mode of Administration

By way of example, a patient in need of pancreatic stem cells as described herein can be treated as follows. Cells of the invention can be administered to the patient, preferably in a biologically compatible solution or a pharmaceutically acceptable delivery vehicle, by ingestion, injection, inhalation or any number of other methods. A preferred method is endoscopic retrograde injection. Another preferred method is injection or placement of the cells or pseudo-islet like aggregates into the space under the renal capsule. The dosages administered will vary from patient to patient; a "therapeutically effective dose" can be determined, for example but not limited to, by the level of enhancement of function (e.g., insulin production or plasma glucose levels). Monitoring levels of stem cell introduction, the level of expression of certain genes affected by such transfer, and/or the presence or levels of the encoded product will also enable one skilled in the art to select and adjust the dosages administered. Generally, a composition including stem cells will be administered in a single dose in the range of $10^5-10^8$ cells per kg body weight, preferably in the range of $10^6-10^7$ cells per kg body weight. This dosage may be repeated daily, weekly, monthly, yearly, or as considered appropriate by the treating physician. The invention provides that cell populations can also be removed from the patient or otherwise provided, expanded ex vivo, transduced with a plasmid containing a therapeutic gene if desired, and then reintroduced into the patient.

Pharmaceutical Compositions

The invention provides for compositions comprising a stem cell according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . . Salts tend to be more soluble in aqueous or other protonic solvents that are the corresponding free base forms. In other cases, the preferred preparation may be a lyophilized powder in 1 mM –50 mM histidine, 0.1%–2% sucrose, 2%–7% mannitol at a Ph range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

The above disclosure generally describes the present invention. A more complete understanding can be obtained by reference to the following specific examples, which are provided herein for purposes of illustration only and are not intended to limit the scope of the invention.

EXAMPLE 1

Isolation of Nestin-Positive Stem Cells from Rat Pancreas.

Rat islets were isolated from the pancreata of 2–3 month old Sprague-Dawley rats using the collagenase digestion method described by Lacy and Kostianovsky. Human islets were provided by the Diabetes Research Institute, Miami, Fla. using collagenase digestion. The islets were cultured for 96 hrs at 37° C. in 12-well plates (Falcon 3043 plates, Becton Dickinson, Lincoln Park, N.J.) that had been coated with concanavalin A. The culture medium was RPMI 1640 supplemented with 10% fetal bovine serum, 1 mM sodium pyruvate, 10 mM HEPES buffer, 100 $\mu$g/ml streptomycin, 100 units/ml penicillin, 0.25 $\mu$g/ml amphotericin B (GIBCO BRL, Life Science Technology, Gaithersburg, Md.), and 71.5 mM $\beta$-mercaptoethanol (Sigma, St. Louis, Mo.).

After 96 hrs, fibroblasts and other non-islet cells had adhered to the surface of concanavalin A coated wells and the islets remained floating (did not adhere to the surface). At this time, the media containing the islets were removed, centrifuged down, and the purged islets replated in 12-well plates without a coating of concanavalin A. The islets were then cultured in the above RPMI 1640 medium supplemented with 20 ng/ml of basic fibroblast growth factor-2 and 20 ng/ml of epidermal growth factor.

The islets adhered to the surface of the plates, and cells grew out and away from the islets in a monolayer. These cells that form a monolayer were nestin-positive by immunostaining with a rabbit anti-rat nestin antiserum developed by Dr. Mario Vallejo at the Massachusetts General Hospital. Other nestin antibodies may be used, for example the R.401 antibody described hereinabove, or the MAB533 antibody. A monoclonal antibody specific for rat embryo spinal cord nestin, MAB353, ATCC No. 1023889; is described in Journal of Neuroscience 1996; 16:1901–100; and also available from Chemicon International, Single Oak Dr., Temecula, Calif. 92590 USA. After two weeks of culture, several (3–5) of the nestin-positive monolayer cells were removed by picking with a capillary tube (cylinder cloning) and were replated on the 12-well plates (not coated with concanavalin A) and cultured in the RPMI 1640 medium further supplemented with bFGF-2 and EGF. The cells propagated at a rapid rate and reached confluence after six days of culture. After 12 days of culture, the cell monolayer formed waves in which they begin to pile up in a co-linear manner. On day 15 of culture, the cell waves began to condense, migrate into spheroid bodies and by day 17 the surface of the wells contained these spheroid bodies (ca. 100 µm in diameter), empty spaces, and a few areas of remaining monolayer cells. Several of these monolayer cells were re-picked and re-cloned and the process described above occurred again in precisely the same temporal sequence.

EXAMPLE 2
Differentiation of Pancreatic Stem Cells to Form Islet

Figure 4A:
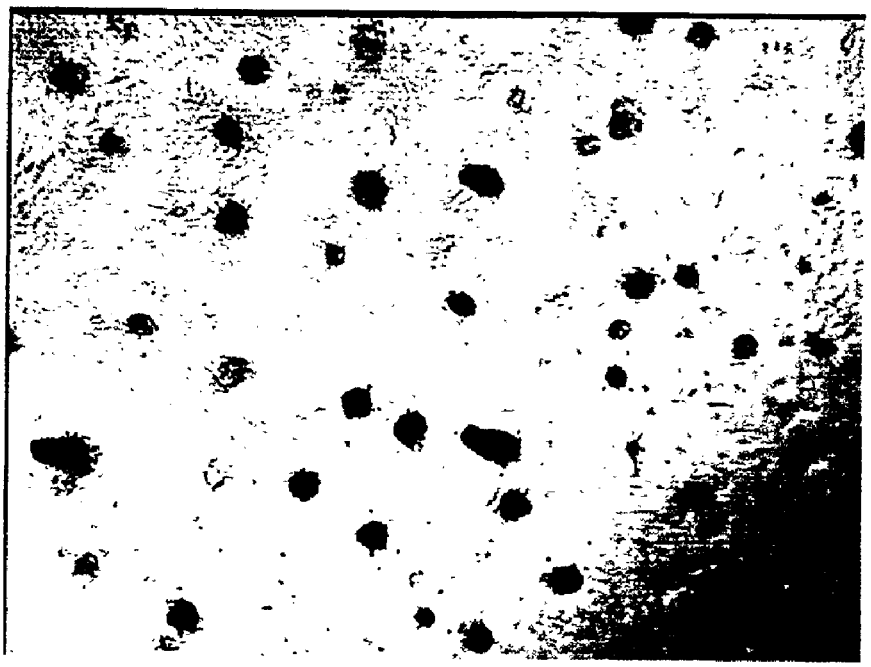
FIG. 4A–4B show the development of islet like structures in culture.
Figure 4B:
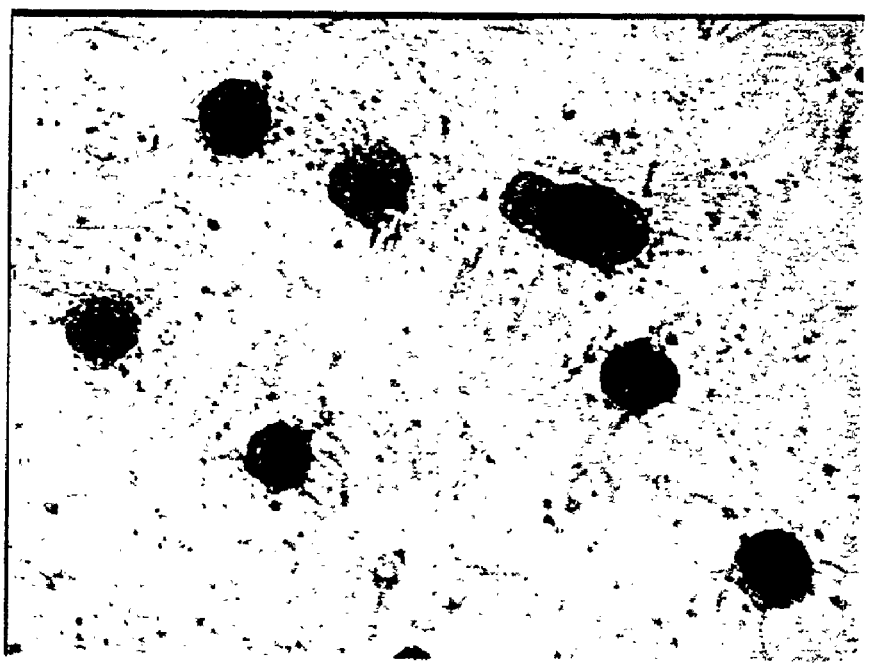
Figure 5:
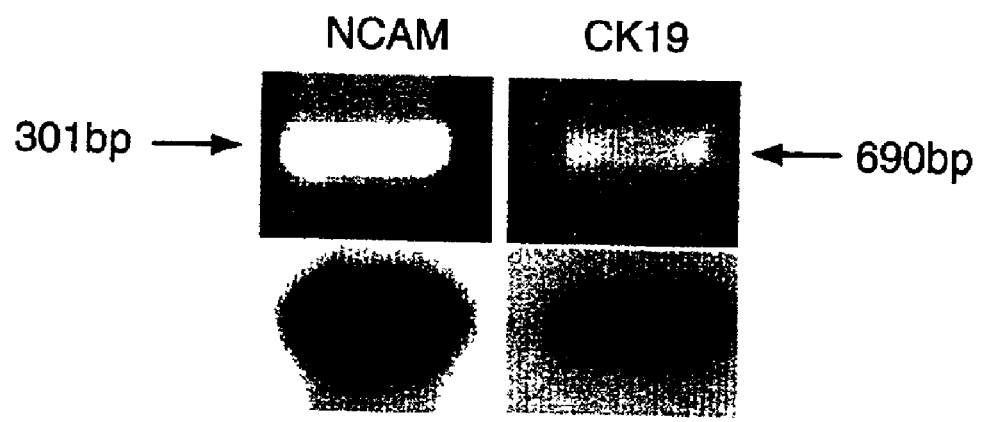
FIG. 5 shows the results of RT-PCR analysis of islet-like structures generated in culture. Expression of NCAM and cytokeratin-19 (CK19) was detected.

Pancreatic islets from rats were first cultured in RPMI medium containing 10% fetal bovine serum using concanavalin-A coated 12-well plates. The islets were maintained in culture for three days in the absence of added growth factors other than those supplied by fetal bovine serum. After this period, during which the islets did not attach, the islets were transferred to fresh plates without concanavalin A. The stem cells were then stimulated to proliferate out from the islets as a monolayer by exposing them to bFGF-2 (20 ng/ml) and EGF (20 ng/ml) for 24 days. After the 24 day period, the monolayer was confluent. Among them was a population of cells surrounding the islets. Cells from that population were picked and subcloned into new 12-well plates and again cultured in the medium containing bFGF and EGF. The subcloned cells proliferated rapidly into a monolayer in a clonal fashion, expanding from the center to the periphery. The cells became confluent at day 6 and then started to form a wave of overlapping cells on day 12. By day 17 the cells migrated almost entirely into spherical structures and tubular structures resembling islet-like structures (pseudo-islet like aggregates) and duct-like structures (pseudo-ducts) (FIG. 4). RT-PCR analysis revealed that the pseudo-islet like aggregates were expressing NCAM (a marker for endocrine cells, see FIG. 5), cytokeratin 19 (a marker for ductal cells, see FIG. 5), and the transcription factor brain-4 (a beta cell marker). Treatment with growth factors is required to achieve terminal differentiation to mature islet cells.

EXAMPLE 3
Isolation and Culture of Human or Rat Pancreatic Islets

Human pancreatic islets were isolated and cultured. Human islet tissue was obtained from the islet distribution program of the Cell Transplant Center, Diabetes Research Institute, University of Miami School of Medicine and the Juvenile Diabetes Foundation Center for Islet Transplantation, Harvard Medical School, Boston, Mass. Thoroughly washed islets were handpicked, suspended in modified RPMI 1640 media (11.1 mM glucose) supplemented with 10% fetal bovine serum, 10 mM HEPES buffer, 1 mM sodium pyruvate, 100 U per mL penicillin G sodium, 100 µg per mL streptomycin sulfate, 0.25 ng per mL amphotericin B, and 71.5 µM β-mercaptoethanol, and added to Falcon 3043 12-well tissue culture plates that had been coated with Concanavalin A (ConA). The islet preparation was incubated for 96 hrs at 37° C. with 95% air and 5% $CO_2$. In these conditions, many islets remained in suspension (floated), whereas fibroblasts and other non-islet cells attached to the substratum. After 96 h of incubation the media containing the suspended islets was carefully removed, the islets were manually picked and resuspended in the modified RPMI 1640 media now further supplemented with 20 ng/mL each of basic fibroblast growth factor (bFGF) and epidermal growth factor (EGF). The islet suspension (containing 20–30 islets per well) was added to 12-well tissue culture plates not coated with ConA. The islets immediately adhered to the surfaces of the plates. Within several days, a monolayer of cells was observed growing out and away from the islets. In certain instances, human-derived cells were cultured in modified RPMI media containing 2.5 mM glucose, and several growth factor combinations that include activin-A (2 nM), hepatocyte growth factor (100 pM), or betacellulin (500 pM). In those experiments in which cells were challenged with 10 mM nicotinamide, the media contained no serum or growth factors.

EXAMPLE 4
Effects of Glucose and GLP-1 on Differentiation of Pancreatic Stem Cells.

Figure 6:
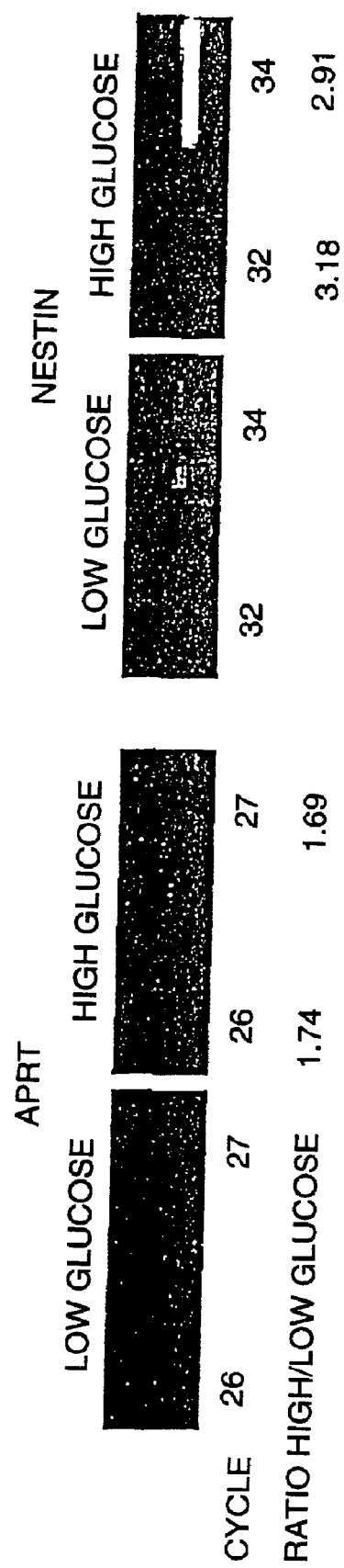
FIG. 6 shows the stimulation of nestin mRNA expression by high glucose. APRT was examined as a control. (SEQ ID NO: 2) (SEQ IS NO: 1)

Elevation of plasma glucose concentration leads to increased pancreatic islet size. The effect of the glucose concentration in the culture medium was therefore investigated using isolated islets, which contain nestin-positive stem cells. Rat pancreatic islets were cultured in a medium containing high (16.7 mM) glucose or in normal (5.6 mM) glucose. After four days, RT-PCR was performed to determine the level of nestin mRNA. The results indicated a three-fold stimulation of nestin mRNA levels in the islets cultured in high glucose compared to the islets cultured in normal glucose (FIG. 6).

Similarly, injection of glucagon-like peptide-1 (GLP-1) into mice was found to increase islet mass by 2-fold in 48 hours. Knockout mice having a disrupted gene for GLP-1 receptor were examined for nestin expression in pancreatic islets. Immunostaining using a nexin antibody was found to be markedly reduced compared to normal mice with GLP-1 receptors.

Animal Model of Diabetes Mellitus

Treatments for diabetes mellitus type that result in relief of its symptoms are tested in an animal which exhibits symptoms of diabetes. It is contemplated that the animal will serve as a model for agents and procedures useful in treating diabetes in humans. Potential treatments for diabetes can therefore be first examined in the animal model by administering the potential treatment to the animal and observing the effects, and comparing the treated animals to untreated controls.

The non-obese diabetic (NOD) mouse is an important model of type I or insulin dependent diabetes mellitus and is a particularly relevant model for human diabetes (see Kikutano and Makino, 1992, Adv. Immunol. 52:285 and references cited therein, herein incorporated by reference). The development of type I diabetes in NOD mice occurs spontaneously and suddenly without any external stimuli. As NOD mice develop diabetes, they undergo a progressive destruction of β-cells which is caused by a chronic autoimmune disease. The development of insulin-dependent diabetes mellitus in NOD mice can be divided roughly into two phases: initiation of autoimmune insulitis (lymphocytic inflammation in the pancreatic islets) and promotion of islet destruction and overt diabetes. Diabetic NOD mice begin life with euglycemia, or normal blood glucose levels, but by about 15 to 16 weeks of age the NOD mice start becoming hyperglycemic, indicating the destruction of the majority of their pancreatic β-cells and the corresponding inability of the pancreas to produce sufficient insulin. In addition to insulin deficiency and hyperglycemia, diabetic NOD mice experience severe glycosuria, polydypsia, and polyuria, accompanied by a rapid weight loss. Thus, both the cause and the progression of the disease are similar to human patients afflicted with insulin dependent diabetes mellitus. Spontaneous remission is rarely observed in NOD mice, and these diabetic animals die within 1 to 2 months after the onset of diabetes unless they receive insulin therapy.

The NOD mouse is used as an animal model to test the effectiveness of the various methods of treatment of diabetes by administering a stem cell preparation according to the invention. As such, treatment via administration of stem cells are tested in the NOD mouse for their effect on type I diabetes.

The stem cells are administered to a NOD mouse, typically intraperitoneally, according to the following dosage amounts. NOD mice are administered about $1 \times 10^1$ to $1 \times 10^4$ cells per mouse. Administration of the cells is started in the NOD mice at about 4 weeks of age, and is continued for 8 to 10 weeks, e.g., 3 times a week. The mice are monitored for diabetes beginning at about 13 weeks of age, being tested twice per week according to the methods described below. The effects of treatment are determined by comparison of treated and untreated NOD mice.

The effectiveness of the treatment methods of the invention on diabetes in the NOD mice is monitored by assaying for diabetes in the NOD mice by means known to those of skill in the art, for example, examining the NOD mice for polydipsia, polyuria, glycosuria, hyperglycemia, and insulin deficiency, or weight loss. For instance, the level of urine glucose (glycosuria) can be monitored with Testape (Eli Lilly, Indianapolis, Ind.) and plasma glucose levels can be monitored with a Glucometer 3 Blood Glucose Meter (Miles, Inc., Elkhart, Ind.) as described by Burkly, 1999, U.S. Pat. No. 5,888,507, herein incorporated by reference. Monitoring urine glucose and plasma glucose levels by these methods, NOD mice are considered diabetic after two consecutive urine positive tests gave Testape values of +1 or higher or plasma glucose levels>250 mg/dL (Burkly, 1999, supra). Another means of assaying diabetes in NOD mice is to examine pancreatic insulin levels in NOD mice. For example, pancreatic insulin levels can be examined by immunoassay and compared among treated and control mice (Yoon, U.S. Pat. No. 5,470,873, herein incorporated by reference). In this case, insulin is extracted from mouse pancreas and its concentration is determined by its immunoreactivity, such as by radioimmunoassay techniques, using mouse insulin as a standard.

In addition to monitoring NOD mice for diabetes in general, the effects of the inventive methods of treatment are also monitored for gene-specific or gene product-specific effects if the stem cells administered were transformed or transfected with a heterologous gene, thereby allowing a correlation to be drawn between expression of the heterologous gene and its effects on diabetes. For example, the presence of the heterologous gene product may be examined by immunohistochemistry of the pancreatic β-cells of NOD mice for the gene product and for insulin. The expression of the patched and smoothened genes is further examined in NOD mouse islets by detection of the RNA transcript for the patched and smoothened receptors. Reverse transcription-polymerase chain reaction (RT-PCR) amplification is performed by known means to amplify a fragment of mouse patched or smoothened cDNA, and analyzed by agarose gel electrophoresis, according to standard means. The identification of the amplified cDNA fragment is confirmed as corresponding to the patched or smoothened RNA by hybridization of the amplified fragment with a radiolabeled internal oligonucleotide probe for the patched or smoothened genes, or by other such methods as known to one skilled in the art.

EXAMPLE 5

Figure 8E:
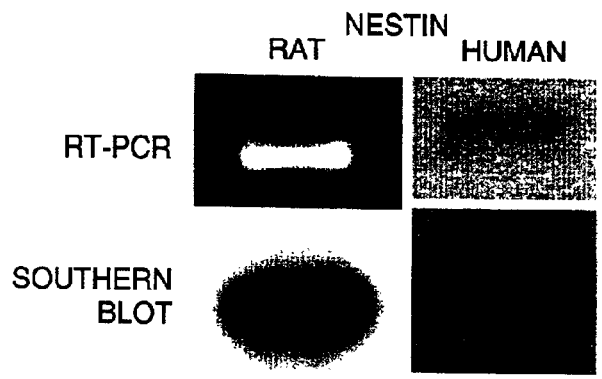

Immunocytochemical Identification of Nestin Positive Human and Rat Pancreatic Stem Cells Pancreatic islets were analyzed for nestin expression. Islets and stem cells were isolated as described above. Nestin expression was observed by immunocytochemical staining in a distinct population of cells within developing islet clusters of embryonic day 16 (E16) rat pancreas (FIG. 8A) and in islets of the adult pancreas (postnatal 60 days) (FIG. 8B). Immunocytochemical staining was performed as follows.

Cryosections (6 μM) prepared from embryonic day 16 and adult (60 day) rat pancreata as well as cells were fixed with 4% paraformaldehyde in phosphate. Cells were first blocked with 3% normal donkey serum for 30 min at room temperature and incubated with primary antisera overnight at 4° C. The antisera were rinsed off with PBS and incubated with the respective Cy-3 and Cy-2 labeled secondary antisera for 1 hour at room temperature. Slides were then washed with PBS and coverslipped with fluorescent mounting medium (Kirkegaard and Perry Labs, Gaithersburg, Md.). Tissue sections were incubated overnight at 4° C. with primary antisera. Primary antisera were then rinsed off with PBS, and slides were blocked with 3% normal donkey serum for 10 min at room temperature before incubation with donkey anti-Cy3 (indocarbocyanine) and either anti-guinea pig (insulin), anti-mouse (glucagon), or anti-sheep (somatostatin) sera DTAF (Jackson Immuno Research Laboratories, West Grove, Pa.) for 30 min at room temperature. Slides were then rinsed with PBS and coverslipped with fluorescent mounting medium (Kirkegaard and Perry Laboratories, Gaithersburg, Md.). Fluorescence images were obtained using a Zeiss Epifluorescence microscope equipped with an Optronics TEC-470 CCD camera (Optronics Engineering, Goleta, Calif.) interfaced with a PowerMac 7100 installed with IP Lab Spectrum analysis software (Signal Analytics Corp, Vienna, Va.).

The nestin-positive cells are distinct from β-, α-, δ-, and PP-cells because they do not co-stain with antisera to the hormones insulin (FIGS. 8A & B), glucagon, somatostatin, or pancreatic polypeptide. The nestin-positive cells also do not co-stain with antisera to collagen IV, a marker for vascular endothelial cells (FIG. 8C) nor with an antiserum to galanin, a marker for nerve cells or a monoclonal antibody to cytokeratin 19, a specific marker for ductal cells (FIG. 8). Nestin-positive staining is associated with distinct cells within the islets clearly observed by nuclear costaining (FIG. 8).

EXAMPLE 6

Identification of Nestin Positive Human and Rat Stem Cells by RT-PCR

To confirm the immunocytochemical identification of nestin expression in pancreatic islets, we performed an RT-PCR of the nestin mRNA using total RNA prepared from freshly isolated rat islets and human islet tissue. RT-PCR was performed according to the following method.

Total cellular RNA prepared from rat or human islets was reverse transcribed and amplified by PCR for 35 cycles as described previously (Daniel et al., 1998, Endocrinology, 139:3721–3729). The oligonucleotides used as primers or amplimers for the PCR and as probes for subsequent Southern blot hybridization are:

| | |
|---|---|
| Rat nestin: | Forward, 5'gcggggcggtgcgtgactac3';<br>(SEQ ID NO: 3);<br>Reverse, 5'aggcaagggggaagagaaggatgt3';<br>(SEQ ID NO: 4);<br>Hybridization, 5'aagctgaagccgaatttccttgggataccag-<br>agga3'.<br>(SEQ ID NO: 5); |
| Rat keratin 19: | Forward, 5'acagccagtacttcaagacc3';<br>(SEQ ID NO: 6);<br>Reverse, 5'ctgtgtcagcacgcacgtta3';<br>(SEQ ID NO: 7);<br>Hybridization, 5'tggattccacaccaggcattgaccatgcca3'.<br>(SEQ ID NO: 8); |
| Rat NCAM: | Forward, 5'cagcgttggagagtccaaat3';<br>(SEQ ID NO: 9);<br>Reverse, 5'ttaaactcctgtggggttgg3';<br>(SEQ ID NO: 10);<br>Hybridization, 5'aaaccagcagcggatctcagtggtgtggaacgat-<br>gat3'.<br>(SEQ ID NO: 11); |
| Rat TDX-1 | Forward, 5'atcactggagcagggaagt3'<br>(SEQ ID NO: 12);<br>Reverse, 5'gctactacgtttcttatct3'<br>(SEQ ID NO: 13);<br>Hybridization, 5'gcgtggaaaagccagtggg3'<br>(SEQ ID NO: 14); |
| Human nestin: | Forward, 5'agaggggaattcctggag3';<br>(SEQ ID NO: 15);<br>Reverse, 5'ctgaggaccaggactctcta3';<br>(SEQ ID NO: 16);<br>Hybridization, 5'tatgaacgggctggagcagtctgaggaaagt3'.<br>(SEQ ID NO: 17); |
| Human keratin: | Forward, 5'cttttcgcgcgcccagcatt3';<br>(SEQ ID NO: 18);<br>Reverse, 5'gatcttcctgtccctcgagc3';<br>(SEQ ID NO: 19);<br>Hybridization, 5'aaccatgaggaggaaatcagtacgctgagg3'.<br>(SEQ ID NO: 20); |
| Human glucagon: | Forward, 5'atctggactccaggcgtgcc3';<br>(SEQ ID NO: 21);<br>Reverse, 5'agcaatgaattccttggcag3';<br>(SEQ ID NO: 22);<br>Hybridization, 5'cacgatgaatttgagagacatgctgaaggg3'.<br>(SEQ ID NO: 23). |

Primers were selected from two different exons and encompassed at least one intronic sequence. In addition, an RT minus control was run for most samples. PCR cycling was at 94° C. for 1 min followed by 94° C. for 10 secs, 58/56° C. for 10 secs, 72° C. for 1 min, 35 cycles, and 72° C. for 2 min. The annealing temperature was 58° C. for rat nestin and 56° C. for the remaining primer pairs.

For Southern hybridization oligonucleotide probes were radiolabeled with T4 polynucleotide kinase and $\gamma^{32}P$ ATP. Radiolabeled probes were hybridized to PCR products that had been transferred to nylon membranes at 37° C. for one hour, then washed in 1×SSC+0.5% SDS at 55° C. for 10–20 min or 0.5×SCC+0.5% SDS at 42° for the human PCR products.

The RT-PCR generated products of the correctly predicted size (FIG. 8E, upper panels) and were confirmed by Southern blotting (FIG. 8E, lower panels) and by DNA sequencing of the products. These data demonstrate the identification of a new cell type in pancreatic islets that expresses nestin and may represent an islet pluripotential stem cell similar to the nestin-positive stem cells in the central nervous system.

EXAMPLE 7
In vitro Proliferation of Nestin Positive Stem Cells

The ability of nestin-positive stem cells to proliferate in vitro was determined.

Figure 9A:
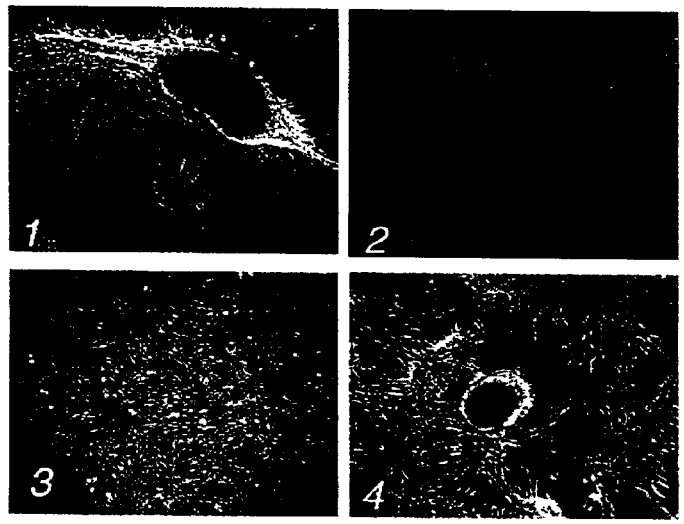
FIG. 9A–9C depict characterization of nestin in stem cells isolated from the pancreas by immunocytochemistry and RT-PCR.
Figure 9B:
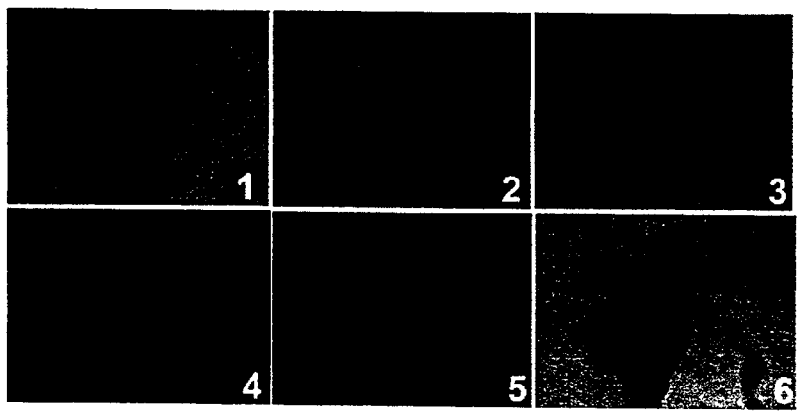

Islets prepared from 60 day-old rats or a normal adult human were first plated on concanavalin-A-coated dishes and cultured in modified RPMI 1640 medium containing 10% fetal bovine serum for four days to purge the islet preparation of fibroblasts and other non-islet cells that adhered to the ConA-coated plates. The islets that did not adhere to the plates under these culture conditions were collected and transferred to 12-well plates (without ConA coating) containing the same modified RPMI 1640 medium now additionally supplemented with bFGF and EGF (20 ng/mL each). The growth factors bFGF and EGF together were selected because they are known to stimulate the proliferation of neural stem cells derived from ependyma of the brain (Reynolds and Weiss, 1996, Dev. Biol., 175:1–13). The islets attached to the plates and cells slowly grew out of the islet as a monolayer (estimated cell doubling time 40–45 hrs in human cells). The outgrowing monolayer of cells were phenotypically homogenous (FIG. 9A, panel 1) and expressed nestin (FIG. 9A, panel 2). Rat cells were picked from the monolayer (batches of at least 20–30 cells), subcloned into 12-well plates, and incubated with the modified RPMI 1640 medium (11.1 mM glucose) containing bFGF and EGF. The subcloned cells grew rapidly and became confluent at six days with an estimated cell doubling time of 12–15 hrs (FIG. 9A, panel 3), and by 12 days formed wave-like structures. After 15–17 days of culture, the cells formed islet-like clusters (ILCs) (FIG. 9A, panel 4). Similar cells were cloned from human islets (FIG. 9B). Upon reaching confluence (FIG. 9B, panel 1), the human cells migrated to form large vacuolated structures in the dish (FIG. 9B, panels 2 and 3). The cells lining the large spaces then changed morphology, rounded, and aggregated together forming three dimensional ILCs (FIG. 9B, panels 4–6).

Figure 9C:
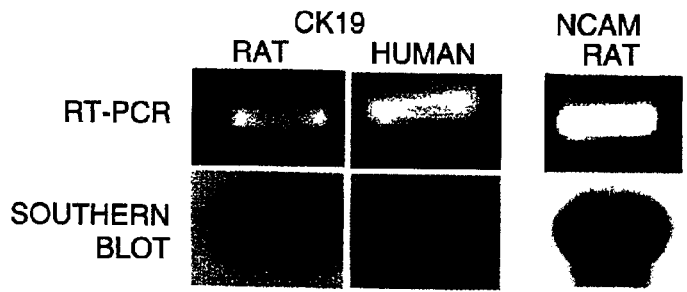

Indicators of differentiation of these nestin-positive islet progenitor cells (NIPs) that formed these ILCs were characterized by RT-PCR and Southern blot and found that they express the endocrine marker NCAM (neural cell adhesion molecule) (Cirulli et al., 1994, J. Cell Sci., 107:1429–36) (FIG. 9C, right panel) and the ductal cell marker CK19 (cytokeratin 19) (Bouwens et al., 1998, J. Pathol., 184:234–9; Bouwens et al., 1995, J. Histochem. Cytochem., 43:245–53; Bouwens et al., 1994, Diabetes, 43:1279–93) (FIG. 9C, left panels). At this stage of the studies it was concluded that when the NIPs became confluent and aggregated into islet-like cell clusters, they began to express pancreatic genes (NCAM and CK19), but were limited in expression of islet genes because of the absence of growth factors essential for their differentiation to endocrine cells. It was also recognized that the differentiation of a progenitor cell population typically requires first a proliferative phase and then quiescence of proliferation in the presence of differentiation-specific morphogen growth factors. Therefore the culture conditions were modified in some instances by replacing the media containing 11.1 mM glucose, bFGF and EGF, which induces proliferation of cells, with media containing lower glucose (2.5 mM), which is less proliferative, and the factors HGF/Scatter Factor or betacellulin and Activin A. Glucose is a known proliferative factor for pancreatic islet β-cells (Swenne, 1992, Diabetologia, 35:193–201; Bonner-Weir, 1989, Diabetes, 38:49–53) and both HGF/Scatter Factor and Activin A have been shown to differentiate the pancreatic ductal cell line AR42J into an endocrine phenotype that produces insulin, glucagon, and other pancreatic endocrine cell proteins (Mashima et al., 1996, Endocrinology, 137:3969–76; Mashima et al., 1996, J. Clin. Invest., 97:1647–54).

Cultures containing ILCs expressed the pancreas-specific homeodomain protein IDX-1 by immunocytochemistry (FIG. 10A, upper panel), RT-PCR and Southern blot (FIG.

10B), and by Western immunoblot (FIG. 10C). The ILCs also expressed the mRNA encoding proglucagon as seen by RT-PCR (FIG. 10D) and produced immunoreactive glucagon, glucagon-like peptide-1, and insulin. Radioimmunoassays of media obtained following 72–96 h of culture of islet-like clusters in several wells gave values of 40–80 pg/ml GLP-1, 30–70 pg/ml glucagon, 29–44 pg/ml insulin. Radioimmunoassays were performed as follows.

Insulin and glucagon concentrations in culture media were determined by ultra sensitive radioimmunoassay kits purchased from Linco Research Inc. and DPC Inc., respectively. The antisera supplied in the respective kits are guinea pig anti-human insulin and rabbit anti-human glucagon. GLP-1 secretion was measured with an anti-human GLP-1 (7–36)amide rabbit polyclonal antiserum raised by immunization of a rabbit with a synthetic peptide CFIAWLVKGR (SEQ ID NO: 54) amide conjugated to keyhole limpet hemocyanin. The antiserum is highly specific for the detection of GLP-1(7–36)amide and only weakly detects proglucagon. The sensitivity levels for these assays are 6 pg/mL, 13 pg/mL and 10.2 pg/mL, respectively.

Incubation of the ILCs for 7 days in 10 mM nicotinamide, as described by Ramiya et al. (Ramiya et al., 2000, Nat. Med., 6:278–282), increased insulin secretion by 2- to 3-fold.

Figure 16:
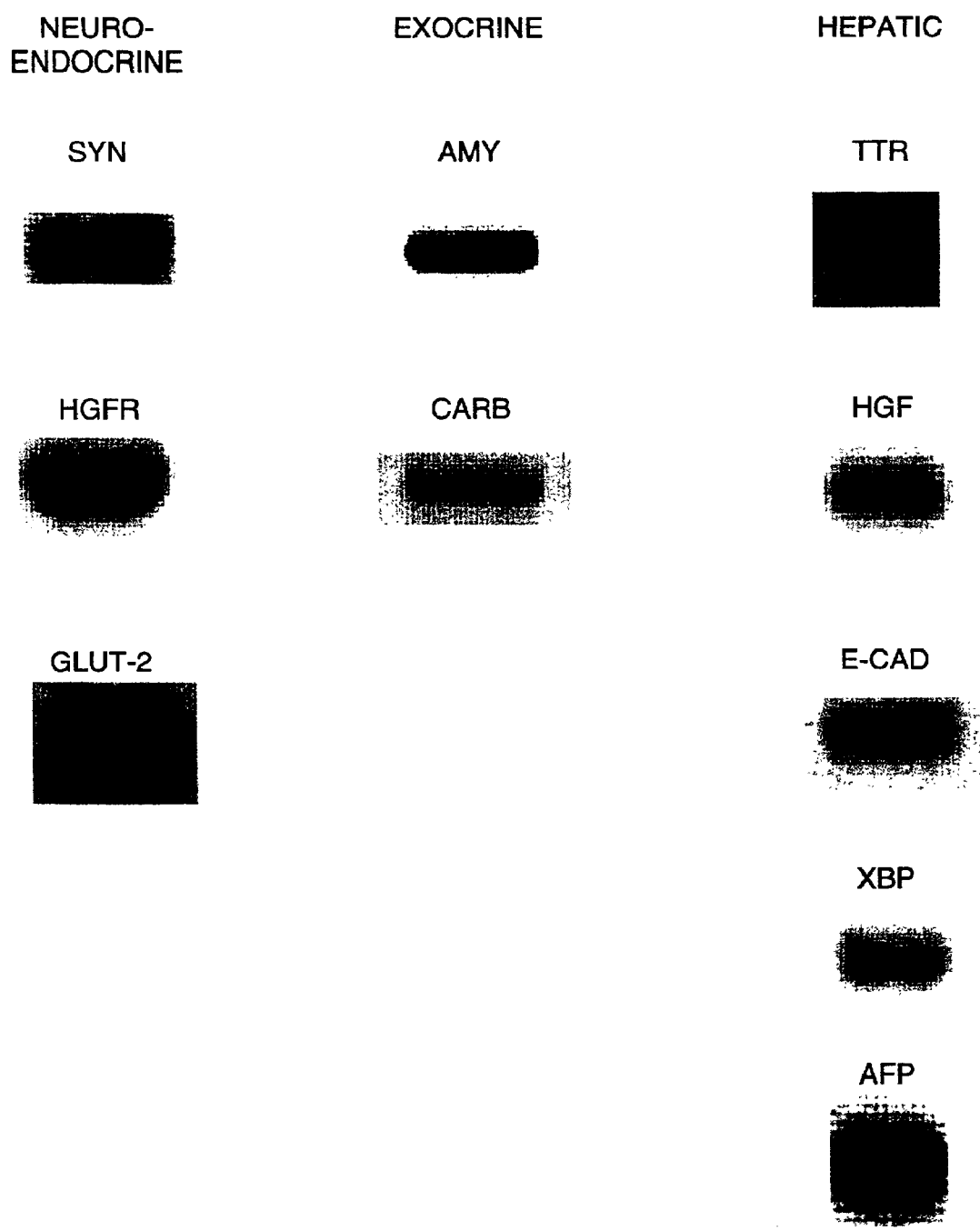
FIG. 16 depicts expression of proglucagon and insulin mRNA as determined by RT-PCR.

Several additional pancreatic markers were expressed in differentiated NIPs such as glucose transporter-2 (Wang et al., 1998), synaptophysin, and HGF (Menke et al., 1999) as shown in FIG. 16. To determine whether the differentiating NIPs may have properties of pancreatic exocrine tissue, we used RT-PCR and detected the expression of amylase and procarboxypeptidase (FIG. 16).

Figure 15A:
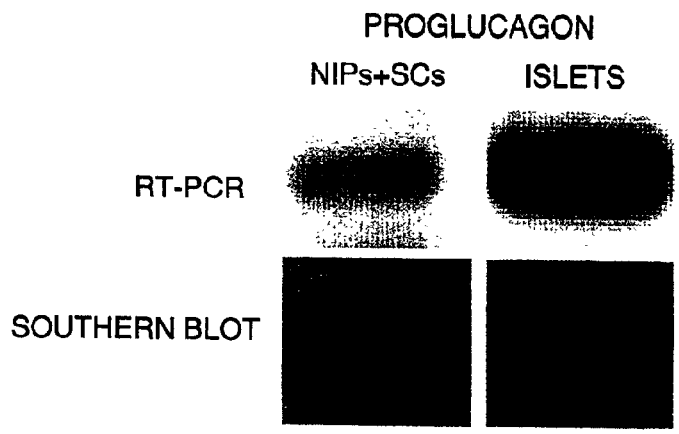
FIG. 15A–15C depict expression of neuroendocrine, exocrine pancreatic and hepatic markers in human NIP cultures containing stem cells.
Figure 15B:
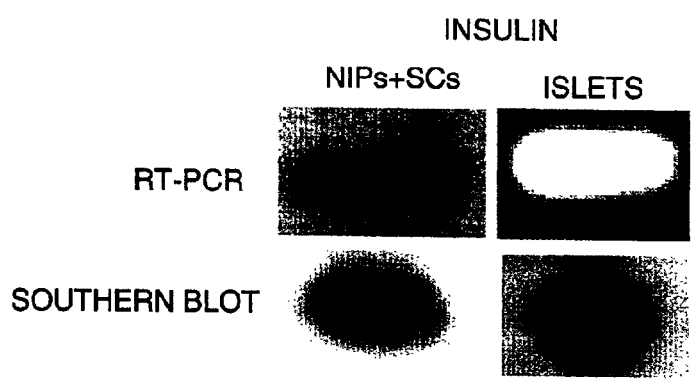
Figure 15C:
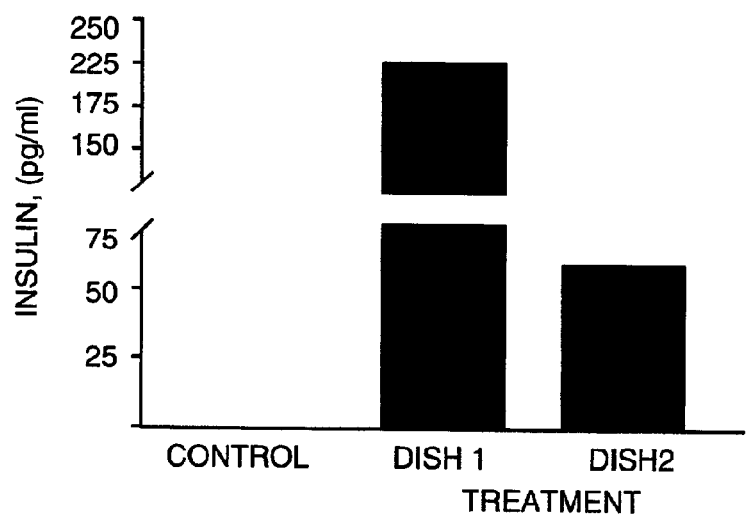

Some cultures of NIPs containing stem cells also expressed the mRNA encoding proglucagon and insulin as seen by RT-PCR (FIGS. 15A and B).

The expression of IDX-1 is of particular importance because it is recognized to be a master regulator of pancreas development, and particularly to be required for the maturation and functions of the pancreatic islet β-cells that produce insulin (Stoffers et al., 1997, Trends Endocrinol. Metab., 8:145–151).

Figure 11A:
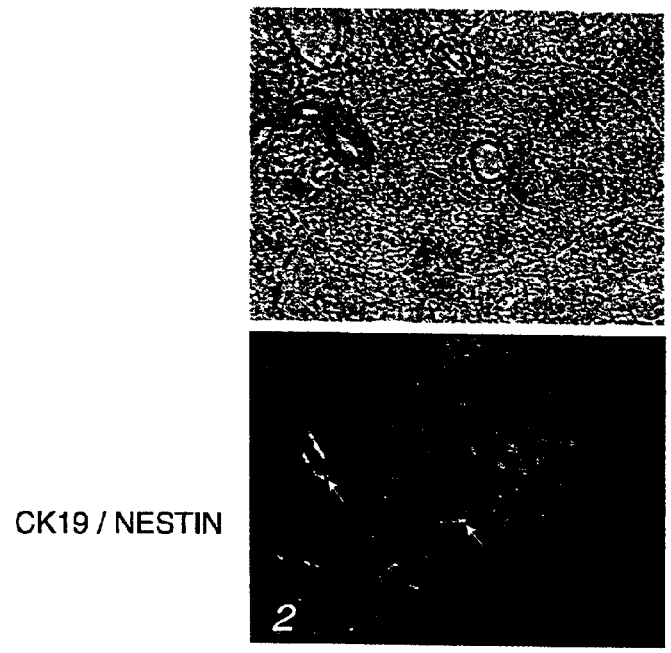
FIG. 11A–11C demonstrate localization of nestin-positive cells to localized regions of the ducts of the rat pancreas.
Figure 11B:
Figure 11C:
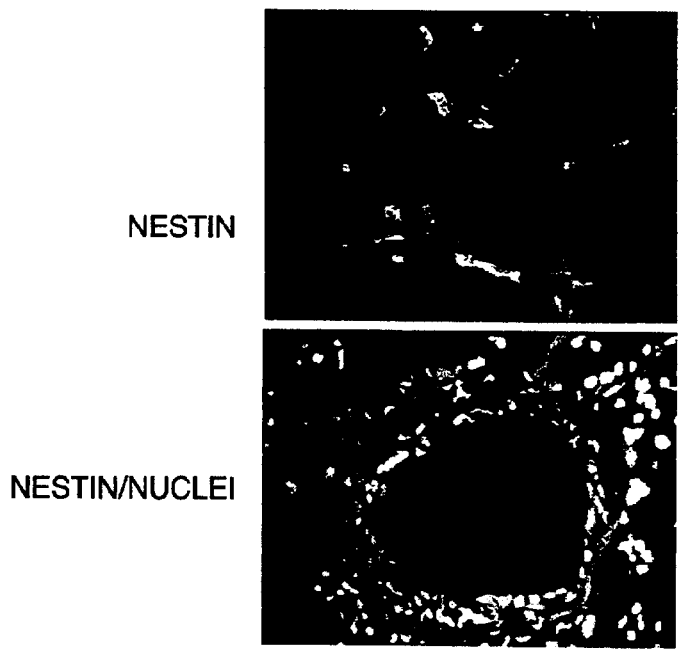

Because the neogenesis of new islets is also known to occur by differentiation of cells in pancreatic ducts, particularly during the neonatal period (rats and mice) but to some extent throughout adult life (Bonner-weir et al., 1993, Diabetes, 42:1715–1720; Rosenberg, 1995, Cell Transplant, 4:371–383; Bouwens et al., 1996, Virchows Arch., 427:553–560), nestin expression was analyzed in the pancreatic ducts of adult rats. By dual fluorescence immunocytochemistry with antisera to nestin and to cytokeratin 19, a marker of ductal epithelium, nestin is strongly expressed in localized regions of both the large and small ducts, as well as in some centrolobular ducts within the exocrine acinar tissue (FIGS. 11A and 11B). Remarkably, the localized regions of nestin expression in the ducts are mostly devoid of staining with the anti CK19 antiserum. Further, the nestin-positive cells in the ducts appear to have a morphology that is distinct from that of the epithelial cells. The epithelial cells consist of a homogenous population of cuboidal, rounded cells, whereas the nestin-positive cells are nucleated, serpiginous and appear to reside in the interstices among or around epithelial cells (FIG. 11C).

Thus, CK19 is not expressed in the majority of ductal cells that express nestin suggesting that these nestin-expressing cells located within the pancreatic ducts are a passenger population of cells distinct from the ductal epithelial cells and are stem cells that have not yet differentiated into a ductal or endocrine phenotype. The finding of localized populations of nestin-expressing cells within the pancreatic ducts and islets of the adult rat pancreas further supports the idea that rat pancreatic ducts contain cells that are progenitors of islet cells (neogenesis), but these progenitors are not a subpopulation of ductal epithelial cells per se.

EXAMPLE 8

Transplantation of Pancreatic Stem Cells Engineered to Express IDX-1 in Human Subjects With Diabetes Mellitus Islets isolated from pig or human donor pancreata, or from pancreatic biopsy of eventual human transplant recipient are cultured ex vivo in conditions that stimulate outgrowth of stem cells. Stem cells are then isolated away from islets (cloned), expanded in vitro in proliferation media containing bFGF-2, EGF, and 11.1 mM glucose, transfected/injected with an expression vector containing DNA encoding transcription factor IDX-1, and transplanted into a diabetic recipient. Alternatively, IDX-1-transfected stem cells are treated with GLP-1, or other differentiation morphogens or growth factors for 1–3 days before transplantation to initiate processes of differentiation of engineered stem cells to β-cells. In one embodiment, stem cells are neither expanded or differentiated prior to administration to the recipient or are only expanded or differentiated prior to administration to the recipient. In one embodiment, GLP-1 is administered to the recipient during and for several days after transplantation to stimulate differentiation of stem cells and encourage successful engraftment. According to this method, xenographs (pig islets) or allographs (human islets from a human donor that is not the recipient), as well as isographs (islets derived from the recipient) are carried out. It is hypothesized that when transplanted to a host recipient the stem cell genetic repertoire is reprogrammed so that the host recognizes the stem cells (in the case of xenographs or allographs) as self, such that immune intolerance and graft rejection and destruction by autoimmunity (type 1 diabetes) does not occur.

EXAMPLE 9

Transplantation of Pancreatic Stem Cells Cultured to Stimulate Expression of IDX-1 in Human Subjects With Diabetes Mellitus Islets isolated as described are cultured ex vivo for several days in conditions that stimulate first the expansion (proliferation) of stem cells that exist within the islets and then the expression of transcription factor IDX-1. The proliferation of stem cells is achieved by culturing the islets in media containing bFGF-2, EGF, and 11.1 mM glucose. Induction of the expression of IDX-1 is achieved by incubation in the presence of GLP-1 and 2 mM glucose. The islets so preconditioned by the treatments described are transplanted to the host recipient. Additionally, the host recipient may be administered GLP-1 during and for several days after the transplantation to further expand and differentiate stem cells to insulin-producing cells to enhance success of engraftment.

According to this method, xenographs (pig islets), allographs (human islets from a human donor that is not the recipient), as well as isographs (islets derived from the recipient) are effectuated.

EXAMPLE 10

Xenogeneic Transplantation of Pancreatic Stem Cells into the Kidney

Human nestin-positive-islet progenitor cells (NIPS) were isolated as described, and transplanted under the renal capsules of eight C57B16 mice that were not immunosuppressed. The transplanted human cells were not rejected by the mouse recipient. Current understanding is that a xenograft, such as human tissue, would be rejected by the mouse within 5–10 days. Contrary to current understanding, we found that in 8 of the 8 non-immunosuppressed mice tested to date, all of the transplants successfully engrafted and proliferated into large masses of tissue engulfing the pole of the kidney by one month (30–38 days) after a transplantation of approximately $10^5$ to $10^6$ cells.

One C57B16 mouse was sacrificed and determined to have a large area of new growth at the site of transplantation. A section of the kidney that included the new tissue was divided into two pieces; one piece was frozen for frozen section histology, and the other piece was fixed in paraformaldehyde for paraffin section histology. Frozen sections were prepared and stained with hematoxylin and eosin (H&E) and antisera to various islet cell antigens.

Examination of the H&E stained kidney section demonstrated the presence of a new growth that was not part of the kidney, exhibiting a pleiomorphic morphology consisting of a mixed mesenchymal and epithelial tissue containing hepatic, neural, ductal, adipodipic and hematopoetic components. Photomicrographs of the kidney section demonstrated that the new growth seemed to be invading the renal parenchyme, and the glomeruli. Specific immunostaining with human-specific (not mouse) antisera revealed cords of immunopositive cells staining for human-specific keratins, vimentin, and the CD45 leukocyte antigen specific for human hematapoetic lymphocytes. The kidney of a second C57B16 mouse also had a similar looking new growth at the site of the NIP transplantation.

The paraffin section of the NIP-engrafted kidney of a C57B16 mouse (the first mouse to be sacrificed) was examined. The tissue block that was examined was from the top of the kidney and showed the foreign tissue to be well contained under the renal capsule with no signs of "invasion" into the renal parenchyma. Notably, amongst the pleiomorphic-looking graft tissues were areas that resembled renal parenchyma. Without being bound to theory one hypothesis is that the graft consists of stem cells trying to differentiate and that the stem cells are not "invading" but simply migrating and proliferating and looking for a niche, i.e. mesenchymal instructions. They may be receiving cues from the kidney and may be attempting to differentiate into kidney. The graft cells may not be malignant, but may be just stem cells attempting to carry out their function.

EXAMPLE 11
Xenogeneic Transplantation of Pancreatic Stem Cells into the Pancreas Human nestin-positive-islet progenitor cells (NIPS) are isolated as described, and transplanted into the pancreas of mice that are not immunosuppressed and are (a) injured by streptozotocin (to produce streptozotocin induced diabetes) treatment or (b) NOD mice in which there is an ongoing islet is with inflammation.

The pancreas of the transplanted animals is examined to determine if the NIPs find their proper niche, receive instructions from the islet region, and differentiate into islet (β-cell) cells.

EXAMPLE 12
Treatment of Diabetes by Xenogeneic Transplantation of Pancreatic Stem Cells Human islets are isolated as described and cultured for several days in vitro to expand the stem cell population. Human NIPS are transplanted to the liver via the portal vein (according to conventional procedures well known in the art for transplantation to the liver.

Alternatively, a population of human NIPs (isolated as described) are introduced into the blood stream. In certain embodiments, the human NIPS are introduced via the pancreatic artery, to direct them to the diabetic pancreas.

A population of control (untransplanted animals) and transplanted animals are analyzed for amelioration of the symptoms of diabetes (e.g. blood glucose levels, insulin levels, number of pancreatic β-cells.

EXAMPLE 13
Identification of Nestin Positive Stem Cells in the Liver

Rat livers were isolated and frozen section were prepared according to methods known in the art and described herein.

Figure 13A:
FIGS. 13A and B depicts immunofluorescent staining of nestin positive liver stem cells.
Figure 13B:
Figure 14:
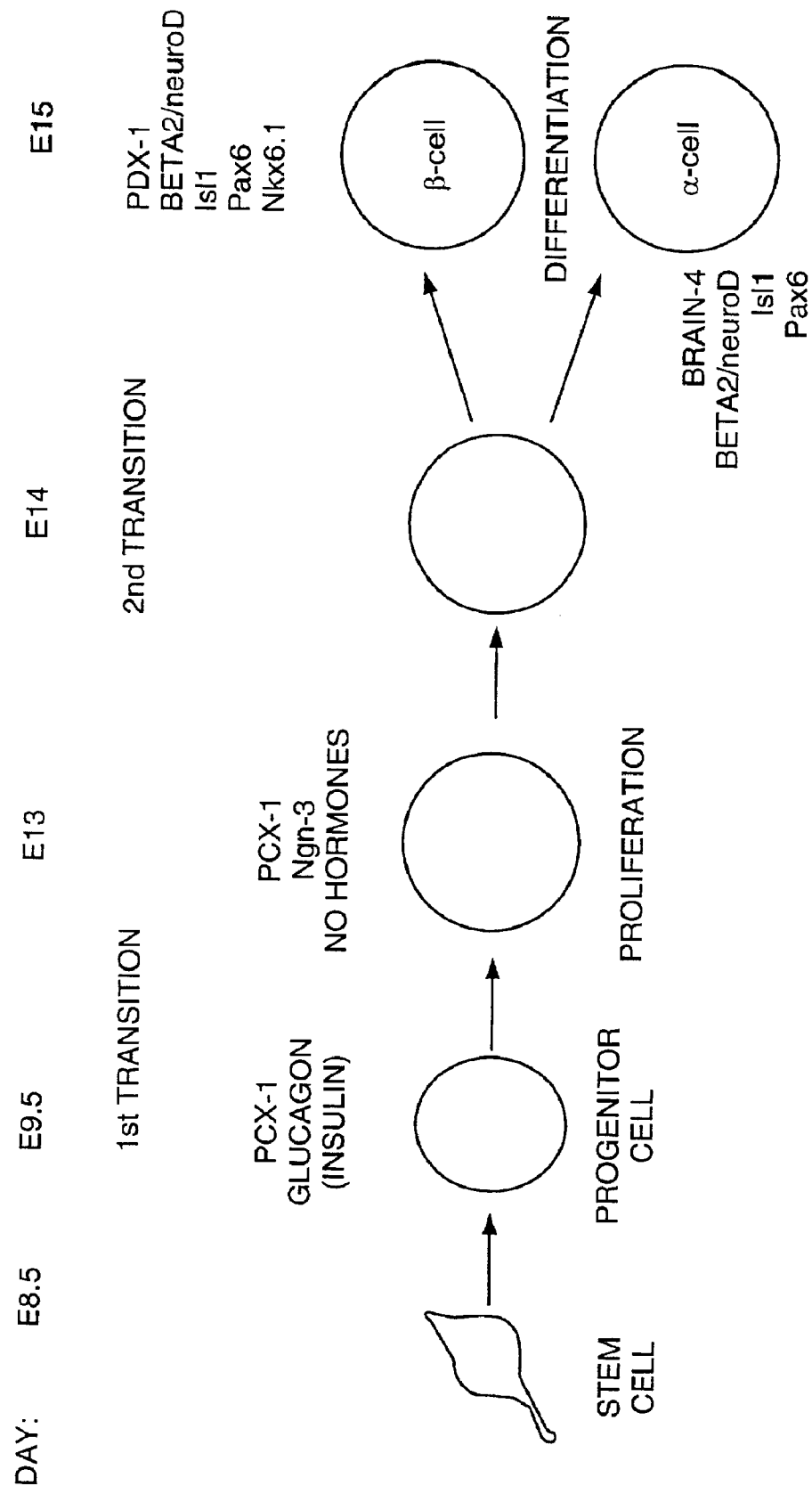
FIG. 14 depicts the sequential appearance of transcription factors during development of the murine endocrine pancreas.

Frozen sections of rat liver (6 μM) were immunostained with a rabbit polyclonal anti-nestin serum. The immunofluorescent signal was developed by reaction of anti-donkey IgG serum tagged with the fluorophore, Cy3 (yellow-orange color. Nestin-positive cells surrounding a possible large biliary duct are depicted in FIG. 13A. Clusters of nestin positive cells surrounding several small biliary ducts are depicted in FIG. 13B.

EXAMPLE 14
Differentiation of NIPs Toward Hepatic Phenotype

Because of the reported apparent commonalties between hepatic stem cells (oval cells), hepatic stellate cells, and progenitor cells in the pancreas, and the observations that following some injuries, the regenerating pancreas undergoes liver metaplasia (Slack, 1995; Reddy et al., 1991; Bisgaard et al., 1991; Rao et al., 1996), we performed RT-PCR to detect liver-expressed genes in the stem cells. PCR products were obtained for XBP-1, a transcription factor required for hepatocyte development (Reimold et al., 2000), and transthyretin, a liver acute phase protein. Several other liver markers were also expressed such as α-fetoprotein (Dabeva et al., 2000), E-Cadherin (Stamatoglou et al., 1992), c-MET (Ikeda et al., 1998), HGF (Skrtic et al., 1999) and synaptophysin (Wang et al., 1998); see FIG. 16)) The expression of proteins shared by the pancreas and liver, such as HGF and synaptophysin, may reflect their common origin from the embryonic foregut endoderm, and represent differentiation toward either pancreatic or hepatic phenotypes.

EXAMPLE 15
A Method for the Use of NIPs to Pre-nduce a State of Immune Tolerance in a Prospective Host Recipient of a Tissue/Organ Graft NIPs are used to pre-induce a state of tolerance toward a potential organ donor. Recent published reports indicate that the transplantation of stem cells from a donor into a transplant recipient can induce tolerance to transplants from the donor without any requirement for immunosuppressive drugs (see for example Fandrich et al., Nat. Med., February 2002, 8:171; Quaini et al., N. Engl. J. Med., 3 Jan. 2002, 346:5; Korbling et al., N. Engl. J. Med., 7 Mar. 2002, 346:738. The procedure described herein corroborates these observations and demonstrates a novel use of NIPs in the pre-induction of a state of immune tolerance toward a potential organ donor, prior to organ transplantation from the donor into the recipient According to this method, a tissue biopsy is obtained from the pancreas or liver of a prospective human donor. Human nestin positive cells (NIPs) are isolated and expanded in vitro, as described, to generate NIPs or NIP equivalent stem/progenitor cells. These NIPs are then administered to an immunologically competent recipient either via subcutaneous or intravenous injection. After 4–8 weeks, tissue specimens are obtained by needle or punch biopsy. Genomic PCR and in situ hybridization using donor-specific probes indicate that the transplanted human NIPs colonize multiple organs of the recipient and created a state of micro/mixed chimerism which induced a condition of immune tolerance. Acceptance of a human tissue graft by a recipient is believed to result from the differentiation of the transplanted stem/progenitor cells into dendritic antigen-presenting cells and so induces the immune system of the recipient to recognize the engrafted human tissue as self. The success of the induction of immune tolerance in the recipient toward the donor tissue is confirmed by taking a skin biopsy from the donor and engrafting it on the skin of the recipient and showing that the recipient does not reject the donor skin graft. After verification of the induction of a state of immune tolerance toward the donor, the NIP transplant is surgically removed. Organs from the donor (kidney, heart, liver, pancreas) are then transplanted into the recipient without incurring rejection of the grafted organ. This organ pre-transplantation protocol commandeers the recipient's immune system to recognize the grafted organ as self and therefore obviates the need for powerful but toxic immuno-suppressive drugs.

References

Bisgaard, H. C. and Thorgeirsson, S. S. 1991. Evidence for a common cell of origin for primitive epithelial cells isolated from rat liver and pancreas. J. Cell Physiol. 147:333–343.

Bjornson, C. R. et al. 1999. Turning brain into blood: a hematopoietic fate adopted by adult neural stem cells in vivo. Science 283:534–537.

Boggs, S. S. 1990. Targeted gene modification for gene therapy of stem cells. Int J. Cell Cloning 8:80–96.

Bouwens, L. et al. 1994. Cytokeratins as markers of ductal cell differentiation and islet neogenesis in the neonatal rat pancreas. Diabetes 43:1279–1283.

Bouwens, L. 1998. Transdifferentiation versus stem cell hypothesis for the regeneration of islet beta cells in the pancreas. Microsc. Res. Tech. 43:332–336.

Cornelius, J. G., et al. 1997. In vitro-generation of islets in long-term cultures of pluripotent stem cells from adult mouse pancreas. Horm. Metab. Res. 29:271–277.

Dahlstrand, J., et al. 1992. Characterization of the human nestin gene reveals a close evolutionary relationship to neurofilaments. J. Cell Sci. 103:589–597.

Dabeva, M. D. et al., 2000. Proliferation and differentiation of fetal liver epithelial progenitor cells after transplantation into adult rat liver. Am. J. Pathol. 156:2017–2031.

Hockfield, S., and McKay, R. D. 1985. Identification of major cell classes in the developing mammalian nervous system. J. Neurosci. 5:3310–3328.

Ikeda et al., 1998. Activated rat stellate cells express c-met and respond to hepatocyte growth factor to enhance transforming growth factor beta1 expression and DNA synthesis. Biochem Biophys Res Commun 250:769–775.

Johansson, C. B. et al. 1999. Identification of a neural stem cell in the adult mammalian central nervous system. Cell 96:25–34.

Karlsson, S. 1991. Treatment of genetic defects in hematopoietic cell function by gene transfer. Blood 78(10): 2481–2492.

Lendahl, U., et al. 1990. CNS stem cells express a new class of intermediate filament protein. Cell 60:585–595.

Miller, A. D. 1990. Retrovirus packaging cells. Hum Gene Therapy 1:5.

Morshead, C. M. et al. 1994. Neural stem cells in the adult mammalian forebrain: a relatively quiescent subpopulation of subependymal cells. Neuron 13:1071–1082.

Rao. M. S. et al., 1996. Expression of transcription factors and stem cell factor precedes hepatocyte differentiation in rat pancreas. Gene Expr 6:15–22.

Reddy, J. K. et al., 1991. Pancreatic Hepatocytes. An in vivo model for cell lineage in pancreas of adult rat. Dig. Dis. Sci. 36:502–509.

Reimold, A. M. et al., 2000 An essential role in liver development for transcription factor XBP-1. Genes Dev. 14:152–7.

Reynolds, B. A. and Weiss, S. 1996. Clonal and population analyses demonstrate that an EGF-responsive mammalian embryonic CNS precursor is a stem cell. Dev. Biol. 175:1–13.

Schiffmann, et. al. 1995. Transfer of the human glucocerebrosidase gene into hematopoietic stem cells of nonablated recipients: successful engraftment and long-term expression of the transgene. Blood 86(3): 1218–1227.

Skrtic, S., et al., 1999. Hepatocyte-stimulated expression of hepatocyte growth formation (HGF) in cultured rat hepatic stellate cells. J. Hepatol. 30:115–124.

Slack, J. M. W., 1995, Developmental Biology of the pancreas. Development, 121:1569–1580.

Stamatoglou, S.C. et al., 1992. Temporal changes in the expression and distribution of adhesion molecules during liver development and regeneration. J. Cell. Biol. 116:1507–1515.

Wang, Z. et al., 1998. GLUT2 in pancreatic islets: crucial target molecule in diabetes induced with multiple low doses of streptozotocin in mice. Diabetes 47:50–56.

Williams, D. A. 1990. Expression of introduced genetic sequences in hematopoietic cells following retroviral-mediated gene transfer. Hum. Gene Therapy 1:229.

Other Embodiments

Other Embodiments are within the claims that follow.

We claim:

1. A method of transplanting an organ in a mammal without the administration of immunosuppressive drugs, comprising the steps of:
   (a) isolating nestin-positive pancreatic stem cells from a pancreatic islet of a mammalian donor;
   (b) transplanting said nestin-positive pancreatic stem cells into a mammalian transplant recipient, wherein said transplanting induces a state of immune tolerance in the recipient toward the donor's stem cells; and
   (c) transplanting an organ from said donor to said recipient, wherein said organ is trasplanted without the administration of immunosuppressive drugs.

2. A method of pre-inducing a state of immune tolerance prior to organ transplantation, comprising the steps of:
   (a) isolating nestin-positive pancreatic stem cells from a pancreatic islet of a mammalian donor; and
   (b) transplanting said nestin-positive pancreatic stem cells into a mammalian transplant recepient, wherein said transplanting induces a state of immune tolerance in the recipient toward the donor's stem cells prior to organ transplantation.

* * * * *